US008163527B2

(12) United States Patent
Tanaka

(10) Patent No.: US 8,163,527 B2
(45) Date of Patent: Apr. 24, 2012

(54) SUBSYSTEMS AND METHODS FOR USE IN PATCH CLAMP SYSTEMS

(75) Inventor: Yokichi J. Tanaka, Foothill Ranch, CA (US)

(73) Assignee: Tecella LLC, Foothill Ranch, CA (US)

(*) Notice: Subject to any disclaimer, the term of this patent is extended or adjusted under 35 U.S.C. 154(b) by 992 days.

(21) Appl. No.: 12/114,474

(22) Filed: May 2, 2008

(65) Prior Publication Data
US 2008/0296175 A1 Dec. 4, 2008

Related U.S. Application Data

(60) Provisional application No. 60/927,810, filed on May 4, 2007, provisional application No. 60/969,275, filed on Aug. 31, 2007, provisional application No. 60/969,378, filed on Aug. 31, 2007, provisional application No. 61/025,650, filed on Feb. 1, 2008.

(51) Int. Cl.
C12N 13/00 (2006.01)
(52) U.S. Cl. ............ 435/173.4; 324/720; 327/362; 327/590; 204/403.1; 205/792
(58) Field of Classification Search .... 435/173.4–173.7; 204/403.01–403.02; 205/792, 777.5; 324/692, 324/76.12, 720; 327/362, 378–388, 551–559, 327/590
See application file for complete search history.

(56) References Cited

U.S. PATENT DOCUMENTS

| 4,441,507 | A | 4/1984 | Steffin |
| 4,510,442 | A | 4/1985 | Neher et al. |
| 5,237,493 | A | 8/1993 | Durig et al. |
| 5,309,085 | A | 5/1994 | Sohn et al. |
| 5,500,188 | A | 3/1996 | Hafeman et al. |
| 6,152,882 | A | 11/2000 | Prutchi |
| 6,163,719 | A | 12/2000 | Sherman et al. |
| 6,380,790 | B1 | 4/2002 | Denison |
| 6,488,829 | B1 | 12/2002 | Schroeder et al. |
| 6,570,432 | B2 | 5/2003 | Denison |
| 6,700,427 | B1 | 3/2004 | Sherman et al. |
| 6,932,893 | B2 | 8/2005 | Bech et al. |
| 7,056,430 | B1 | 6/2006 | Osipchuk et al. |
| 2002/0063067 | A1 | 5/2002 | Bech et al. |
| 2003/0070923 | A1 | 4/2003 | Schroeder et al. |
| 2004/0234943 | A1 | 11/2004 | Lepple-Wienhues |
| 2005/0029099 | A1 | 2/2005 | Eversmann et al. |
| 2005/0158845 | A1 | 7/2005 | Wikswo et al. |
| 2005/0266478 | A1 | 12/2005 | Huang et al. |
| 2006/0194255 | A1 | 8/2006 | Finkel |

(Continued)

FOREIGN PATENT DOCUMENTS
EP 1271144 1/2003

OTHER PUBLICATIONS

International Search Report for International Application No. PCT/US2008/062468, mailed Nov. 19, 2008, 7 pages.

(Continued)

Primary Examiner — J. Christopher Ball
(74) Attorney, Agent, or Firm — Goodwin Procter LLP

(57) ABSTRACT

Subsystems and methods for use in patch clamp systems are provided. For example, in certain embodiments, compensation circuitry is used to compensate for non-idealities present in the patch clamp system. The accuracy of this compensation may be verified by employing, for example, circuitry that models the patch clamp system.

45 Claims, 21 Drawing Sheets

U.S. PATENT DOCUMENTS

2007/0163894 A1      7/2007    Wang et al.

OTHER PUBLICATIONS

Written Opinion for International Application No. PCT/US2008/062468, mailed Nov. 19, 2008, 13 pages.

"Current Clamping Improvements" [online] The Cairn Research Optopatch Instruction Manual, Summer 2004, Cairn Research Ltd.: Kent, UK [retrieved Apr. 29, 2008] Retrieved from the Internet:<http://www.cairnweb.com/manuals/patchman/iclamp.html>, 5 pages.

Benny, "Application of the stretched exponential function to fluorescence lifetime imaging" [online] Biophysical Journal [retrieved Apr. 24, 2008] Retrieved from the Internet: <http://findarticles.com/p/articles/mi_qa3938/is_200109/ai_n8958198/print>, 9 pages.

Halliwell et al. "Chapter 2: Voltage Clamp Techniques" [online] Microelectrode Techniques, The Plymouth Workshop Handbook, 2nd Edition, Edited by D.C. Ogden, Company of Biologists: Cambridge, UK, 1994 [retrieved Apr. 29, 2008] Retrieved from the Internet: <http://www.utdallas.edu/~tres/microelectrode/microelectrodes_ch02.pdf>, pp. 17-35, 19 pages.

Mergler "Patch-clamp technique" [online] Stefan's Homepage [retrieved Apr. 29, 2008] Retrieved from the Internet: <http://www.stefanmergler.de/ptechn_e.htm>, 8 pages.

Sherman et al. "Series Resistance Compensation for Whole-Cell Patch-Clamp Studies Using a Membrane State Estimator" Biophysical Journal, vol. 77, Nov. 1999, pp. 2590-2601, 12 pages.

Ypey et al. "The Basics of Patch-Clamping Explained With Simple Electrical Equivalent Circuits" [online] International School of Biophysics A. Bosellino, 33rd Workshop: Channels and Transporters, May 31-Jun. 6, 2005, Ettore Majorana Foundation and Center for Scientific Culture, Erice, Sicily, Italy [retrieved Apr. 29, 2008] Retrieved from the Internet: <https://medschool.mc.vanderbilt.edu/channels.transporters2005/text/Erice05IntroDemoLect_13347A.pdf>, 35 pages.

Invitation to Pay Additional Fees and Partial Search Report for International Application No. PCT/US2008/062468, mailed Jul. 30, 2008, 9 pages.

Hu et al. "Designing a Signal Conditioning System with Software Calibration for Resistor-feedback Patch Clamp Amplifier," Proc. of the IEEE Engineering in Medicine and Biology, 27th Annual Conference, Sep. 1-4, 2005, pp. 6729-6732.

Kang et al., "Low Noise Design of Patch Clamp Amplifier," Engineering in Medicine and Biology Society, Proceedings of the Twelfth Annual International Conference of the IEEE, Philadelphia, PA, USA, Nov. 1-4 1990, pp. 1103-1104.

Sala et al. "Sources of errors in different single-electrode voltage-clamp techniques: a computer simulation study," Journal of Neuroscience Methods, Elsevier Science Publisher B.V., Amsterdam, NL, vol. 53, No. 2, Aug. 1, 1994, pp. 189-197.

Sherman-Gold, "The Axon Guide for Electrophysiology and Biophysics Laboratory Techniques, Ch.3," Axon Instruments Inc., Jun. 1993, pp. 56-63.

Poindessault et al. "Voltage Clamp With Double Sucrose Gap Technique: External Series Resistance Compensation," Biophysical Journal, vol. 16, 1976, pp. 105-120.

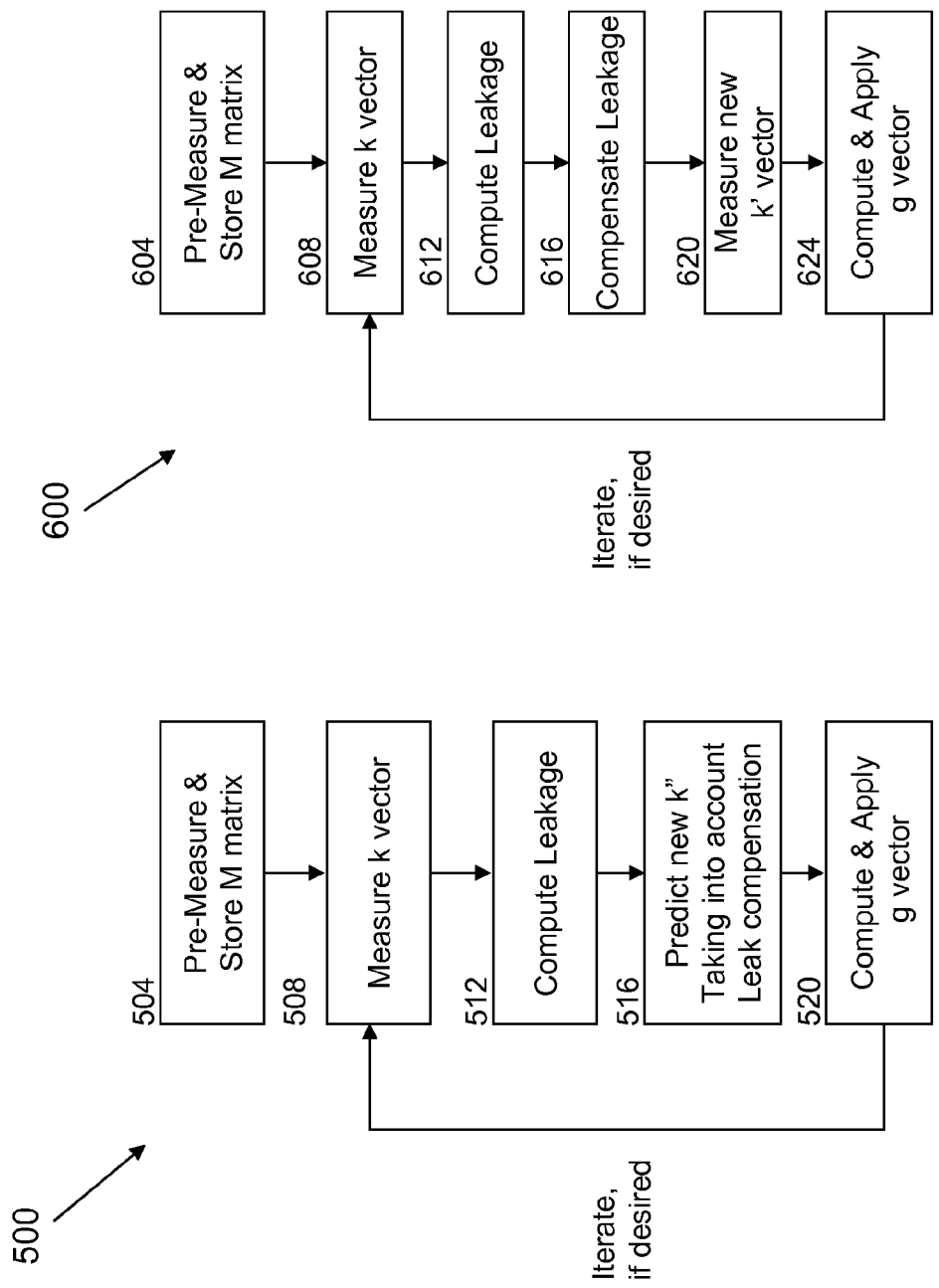

$$\begin{pmatrix} a_0 & b_0 & c_0 & d_0 & e_0 \\ a_1 & b_1 & c_1 & d_1 & e_1 \\ a_2 & b_2 & c_2 & d_2 & e_2 \\ a_3 & b_3 & c_3 & d_3 & e_3 \\ a_4 & b_4 & c_4 & d_4 & e_4 \end{pmatrix} \begin{pmatrix} g_a \\ g_b \\ g_c \\ g_d \\ g_e \end{pmatrix} = \begin{pmatrix} k_0 \\ k_1 \\ k_2 \\ k_3 \\ k_4 \end{pmatrix}$$

Matrix M      g vector      k vector

FIG. 12

SUBSYSTEMS AND METHODS FOR USE IN PATCH CLAMP SYSTEMS

CROSS-REFERENCE TO RELATED APPLICATIONS

This application claims priority to and the benefit of, and incorporates herein by reference in their entirety, U.S. Provisional Patent Application No. 60/927,810, which was filed on May 4, 2007, U.S. Provisional Patent Application No. 60/969,275, which was filed on Aug. 31, 2007, U.S. Provisional Patent Application No. 60/969,378, which was filed on Aug. 31, 2007, and U.S. Provisional Patent Application No. 61/025,650, which was filed on Feb. 1, 2008.

TECHNICAL FIELD

The present invention relates, in various embodiments, to subsystems and methods for use in patch clamp systems.

BACKGROUND

The electrical behavior of cells and cell membranes is often of interest in basic research, as well as in modern drug development. For example, in electrophysiological experiments, electrical measurements are typically made on biological cells and cell membranes in order to understand interactions between specific membrane components. Such measurements may be performed on living cells, membranes, and/or vesicles, as well as on artificial membranes.

"Patch clamping" is one useful technique that is often used to make such measurements. FIG. 1 depicts an exemplary planar patch clamp 2 that is typically used in automated patch clamp systems. As illustrated, the planar patch clamp 2 includes a first chamber 4, a second chamber 8, and a hole 12 that fluidly connects the first and second chambers 4, 8. A biological cell 16 may be deposited inside the first chamber 4 and drawn to the hole 12, for example through the use of differential pressure applied between the first and second chambers 4, 8. A seal 20 of high electrical resistance (e.g., in the range of several hundred MΩ to greater than 1 GΩ) may then be formed between a bottom surface 24 of the first chamber 4 and the biological cell membrane 28. With such a high electrical resistance level for the seal 20 and by rendering permeable the portion 48 of the cell membrane 28 separating the first and second chambers 4, 8 (i.e., the portion 48 of the cell membrane 28 in contact with the hole 12), as described below, it is possible to isolate and measure typical physiological cell 16 currents by controlling the voltage across the cell membrane 28.

Typically, the first chamber 4 is filled with an extracellular ionic solution 32. The second chamber 8 may be filled with a saline buffer solution 34 that may contain a proper concentration of antibiotics. As illustrated, a measurement circuit is typically implemented through the use of a sensing electrode 36 in contact with the extracellular ionic solution 32, a bath electrode 40 connected to ground and in contact with the saline buffer solution 34, and an operational amplifier 44 connected to the sensing electrode 36.

Once the high-resistance seal 20 is achieved between the bottom surface 24 of the first chamber 4 and the biological cell membrane 28, the portion 48 of the cell membrane 28 separating the first and second chambers 4, 8 (i.e., the portion 48 of the cell membrane 28 in contact with the hole 12) may be permeabilized (e.g., electrically, through negative pressure, or through the use of antibiotics) so as to effectively place the bath electrode 40 inside the cell 16. This, in turn, allows for an external voltage command 52 to be placed between the sensing electrode 36 and the bath electrode 40, thereby providing for control of the cell's transmembrane voltage potential (i.e., one may achieve a voltage clamp of the cell's membrane 28). The current flowing in the measurement circuit (i.e., the current flowing through the cell membrane 28) may then be sensed by the operational amplifier 44. That current may also be subsequently recorded and analyzed by a computer controlled data acquisition and recording system 56.

Using the planar patch clamp 2 in an automated patch clamp system typically gives rise, however, to many sources of stray capacitance. Moreover, because the planar patch clamp system 2 is typically used to measure very low cell 16 current (i.e., in the pico-ampere to nano-ampere range), a very high gain resistor 58 (e.g., 10 MΩ to 10 GΩ) is often used in connection with the operational amplifier 44. As such, even very small capacitances (i.e., in the pico-farad range) that occur in the planar patch clamp 2 before the operational amplifier 44 result in very large current spikes.

Two sources of capacitance are particularly troublesome for the planar patch clamp system 2. First, it is often desirable (e.g., when scaling to larger systems having a large number of channels) to locate the operational amplifier 44 away from the first and second chambers 4, 8. Doing so, however, requires a longer cable to connect the sensing electrode 36 to the amplifier 44. But, increasing the cable length also increases the stray capacitance present in the system 2. Second, the cell membrane 28 introduces capacitive spikes into the system 2. The capacitive spikes introduced into the system 2 are much greater (e.g., up to two orders of magnitude greater), however, when multiple cells 16 are probed, rather than just a single cell 16 as illustrated in FIG. 1. Typically, the shape of the aggregate waveform of capacitive spikes that results from multiple cells 16 can not be matched and offset by a simple decay curve, thereby making it difficult to effectively compensate for such capacitive spikes using conventional methods. In addition to the cable and the cell membrane(s) 16, other sources of capacitive spikes within the planar patch clamp system 2 include, for example, electronic components (e.g., the electronics for the operational amplifier 44), printed circuit boards, connectors (e.g., relays or switches), the sensing electrode 36, and the cell holder (or chip) (i.e., the extracellular solution 32 within the first chamber 4).

Several patch clamp systems attempt to compensate for the stray capacitances introduced therein. For example, some systems employ analog compensation. In these systems, a spike having approximately the same magnitude, duration, and time constant as the capacitive spike inherent in the patch clamp system, but with inverse polarity, is generated and added to the input of the operational amplifier 44 to cancel out the inherent capacitive spike. Two benefits of this analog compensation are that the output of the amplifier 44 will not saturate from the inherent capacitive spikes, and increasing the number of amplifier channels will not increase the computational load on the computer controlled data acquisition and recording system 56 since the compensation is done in analog.

Other systems employ digital compensation. In these systems, a reference waveform is recorded, digitized, and stored. Then, during an electrophysiological experiment, the stored reference waveform is scaled and subtracted by the computer controlled data acquisition and recording system 56 following analog-to-digital conversion of the waveform output from the operational amplifier 44. While digital compensation has the benefit of requiring fewer analog components, digital compensation is typically less accurate than analog compensation over a wide range of stimulus voltages. In addition, as the number of amplifier channels increases, system performance suffers when digital compensation is employed as a greater load is placed on the computer controlled data acquisition and recording system 56. Moreover, with digital compensation, the potential for the inherent capacitive spikes to saturate the amplifier 44 output remains.

Regardless, however, of whether analog or digital compensation is employed, known patch clamp systems do not reliably and effectively verify the accuracy of the capacitance compensation, and are not flexibly designed so as to be employed in either a single-cell or multiple-cell configurations (the capacitive spikes in the system varying greatly between the two configurations).

In addition, patch clamp systems 2 that measure ionic current in biological preparations are often compromised by a series resistance ("Rs"), for example the series resistance in a measuring device such as the sensing electrode 36. Rs compensation circuits have been developed in an attempt to maintain a desired clamping voltage in the presence of this undesired series resistance.

One such exemplary Rs compensation circuit 60 is shown in FIGS. 2A and 2B. An object under test, for example the biological cell 16 having a membrane capacitance Cm, a membrane voltage Vm, a membrane current Im, and a membrane resistance Rm, is probed by the sensing electrode 36, which has a series resistance Rs, an electrode voltage Vp, and an electrode current Ip. Measurement circuitry 70, which may include the voltage clamp amplifier 44, a difference amplifier 75, and the current-to-voltage gain resistor 58, measures the electrode current Ip to produce a measured electrode current Ipmeas. A scalar 80 then multiples the measured electrode current Ipmeas to produce an Rs compensation signal Vcomp, which is then added by a voltage summer 90 to a command voltage Vc to produce a clamping voltage Vc'. As will be understood by one skilled in the art, by applying a scaled value of the measured electrode current Ipmeas as positive feedback, the effective value of the sensing electrode 36 series resistance Rs is reduced (i.e., the undesired series resistance Rs is compensated), such that the membrane voltage Vm approximately tracks the command voltage Vc even when the membrane current Im increases substantially.

A significant drawback, however, of the Rs compensation circuit 60 illustrated in FIGS. 2A and 2B is that the positive feedback loop is inherently unstable, causing undamped oscillations to occur as one begins to approach full (i.e., 100%) compensation of the undesired series resistance Rs. In reality, the undamped oscillations begin to occur even as early as once one reaches approximately 70% to 80% compensation of the undesired series resistance Rs. Accordingly, compensation of only approximately 70% to 80% of the undesired series resistance Rs using the Rs compensation circuit 60 illustrated in FIGS. 2A and 2B is achievable in practice.

SUMMARY OF THE INVENTION

The present invention, in various embodiments, addresses the aforedescribed shortcomings of the prior art. For example, in one embodiment, a patch clamp system employs model circuitry to model the stray capacitances present in the patch clamp system and, using that model circuitry, verifies the accuracy of the capacitance compensation. In addition, in various embodiments, the patch clamp system is flexibly designed so as to accurately measure the membrane current of either a single cell or multiple cells. In other words, the patch clamp system is designed so as to effectively and reliably compensate for both the capacitive spikes that originate in the single-cell configuration and the differing capacitive spikes that originate in the multiple-cell configuration. As such, the same patch clamp system may be used in either configuration.

In addition, in another embodiment, the patch clamp system described herein employs an Rs compensation circuit that is capable of providing substantially full (i.e., 100%) compensation of the undesired series resistance Rs in a measuring electrode. Optionally, as described herein, leak current compensation may complement this Rs compensation without interfering with the Rs compensation.

In addition still, other embodiments of the present invention provide improved systems and methods for measuring a characteristic of a cell, such as its current, and for determining and compensating for a capacitance of a device used to hold the cell in an electrophysiological experiment.

In general, in one aspect, embodiments of the invention feature a subsystem for compensating a patch clamp system used in electrophysiological experiments. The subsystem may include model circuitry configured to model at least a portion of the patch clamp system, and compensation circuitry for compensating non-idealities. The compensation circuitry may be configured to be calibrated with at least one first calibration value to compensate for non-idealities introduced by the model circuitry and with at least one second calibration value to compensate for non-idealities introduced by the patch clamp system. The subsystem may also include measurement circuitry that is configured to measure a characteristic of at least one cell while receiving input from the compensation circuitry to compensate for non-idealities introduced by the patch clamp system. In addition, the subsystem may also include a verification module configured to verify, following the measurement of the cell's characteristic, that the compensation circuit, re-calibrated with the at least one first calibration value, compensates for the non-idealities introduced by the model circuitry. In one embodiment, this subsystem is adapted for use with a patch clamp system that includes a test head, a main amplifier, and a long cable therebetween. In such a case, the model circuitry, the compensation circuitry, and the measurement circuitry may all be located within the main amplifier. Ultra-low capacitance switches may also be used within the main amplifier.

In general, in another aspect, embodiments of the invention feature a method for compensating a patch clamp system used in electrophysiological experiments. In accordance with the method, a compensation circuit may be calibrated with at least one first calibration value to compensate for non-idealities introduced by model circuitry that models at least a portion of the patch clamp system. Then, a characteristic of at least one cell may be measured while employing the compensation circuit, re-calibrated with at least one second calibration value, to compensate for non-idealities introduced by the patch clamp system. Following the measurement of the cell's characteristic, it is verified that the compensation circuit, further re-calibrated with the at least one first calibration value, still compensates for non-idealities introduced by the model circuitry.

In various embodiments, the model circuitry is activated prior to calibrating the compensation circuitry with the first calibration value(s), de-activated prior to measuring the characteristic of the cell(s), and re-activated following the measurement of the characteristic. The current exhibited by the cell(s) may be the characteristic that is measured.

In one embodiment, the compensation circuitry is calibrated with the first calibration value(s) to compensate for stray capacitances introduced by the model circuitry. For example, the compensation circuitry may be calibrated with the first calibration value(s) to compensate for stray capacitances introduced by model circuitry of a long cable, model circuitry of a long cable in series with a single cell, and/or model circuitry of a long cable in series with multiple cells. In another embodiment, the compensation circuitry is re-calibrated with the second calibration value(s) prior to measuring the characteristic of the cell(s) to compensate for stray capacitances introduced by the patch clamp system. For example, the compensation circuitry may be re-calibrated with the second calibration value(s) to compensate for stray capacitances introduced by a long cable in the patch clamp system, a long cable in series with a single cell in the patch clamp system, and/or a long cable in series with multiple cells in the patch clamp system. In yet another embodiment, the compensation circuitry is re-calibrated with the second calibration value(s) prior to measuring the characteristic of the cell(s) to compensate for leakage resistance introduced by the patch clamp system. The first and second calibration values may be compared to verify compensation for the non-idealities introduced by the patch clamp system. In addition, the measurement circuitry may include an amplifier whose gain is increased after the compensation circuitry is re-calibrated with the second calibration value(s).

In one embodiment, a stray capacitance introduced by a component in the patch clamp system (e.g., a long cable, a long cable in series with a single cell, and/or a long cable in series with multiple cells) is measured. The verification module may then compare the measured stray capacitance to a capacitance value modeled by the model circuitry to verify compensation for the non-idealities introduced by the patch clamp system. In one embodiment, the measurement circuitry discontinues measuring the characteristic of the cell(s) if the measured stray capacitance value differs from the capacitance value modeled by the model circuitry by more than a predetermined amount.

In general, in yet another aspect, embodiments of the invention feature a subsystem for determining a characteristic of a cell. The subsystem may include sensing circuitry configured to measure a natural resting potential of a cell, a memory configured to store the measured natural resting potential, and clamping circuitry. The clamping circuitry may be configured to alternately apply to the cell i) a first voltage substantially equal to the measured natural resting potential and ii) a second voltage substantially equal to a sum of the measured natural resting potential and a step voltage. The clamping circuitry may also be configured to measure the characteristic of the cell. In one embodiment, the sensing circuitry and the clamping circuitry are each coupled to a common single probe.

In general, in still another aspect, embodiments of the invention feature a method for determining a characteristic of a cell. In accordance with the method, a natural resting potential of a cell may be measured, the measured natural resting potential may be stored in memory, first and second voltages may be alternately applied to the cell, and a characteristic of the cell may be measured. The first applied voltage may be substantially equal to the measured natural resting potential, while the second applied voltage may be substantially equal to a sum of the measured natural resting potential and a step voltage.

In various embodiments, a different step voltage is applied on each application of the second voltage. In addition, the characteristic of the cell may be measured during each application of the second voltage. The measured characteristic may be cell current. A single probe may be employed to measure both the natural resting potential of the cell and the characteristic of the cell.

In general, in a further aspect, embodiments of the invention feature a subsystem for determining a capacitance of a device used to hold a cell in an electrophysiological experiment. The subsystem may include a force amplifier configured to apply a stimulus to the device, a separate sense amplifier configured to measure a response to the stimulus, and a determination module configured to determine the capacitance of the device by analyzing the response to the stimulus.

In general, in another aspect, embodiments of the invention feature a method for determining a capacitance of a device used to hold a cell in an electrophysiological experiment. In accordance with the method, a stimulus may be applied to the device through a force amplifier, a response to the stimulus may be measured with a separate sense amplifier, and the capacitance of the device may be determined by analyzing the response to the stimulus.

In various embodiments, determining the capacitance of the device includes calculating an RC time constant of the response to the stimulus. Compensation circuitry may be employed to compensate for the capacitance of the device.

In general, in yet another aspect, embodiments of the invention feature a patch clamp system for determining a characteristic of at least one cell in an electrophysiological experiment. The patch clamp system may include a device for applying a stimulus to the cell, measurement circuitry for measuring the characteristic of the cell, and first, second, and third compensation circuitry. The first compensation circuitry may be for applying to the measurement circuitry a first compensation signal to compensate for a leakage resistance introduced by the patch clamp system, while the second compensation circuitry may be for applying to the measurement circuitry a second compensation signal to compensate for a series resistance introduced by the device that applies the stimulus to the cell. For its part, the third compensation circuitry may be for applying to the second compensation circuitry a third compensation signal that removes from the measured characteristic of the cell the effect thereon of the first compensation signal. In one embodiment, the second compensation signal is related to the measured characteristic of the cell and the third compensation signal.

In general, in still another aspect, embodiments of the invention feature a method for determining a characteristic of at least one cell in an electrophysiological experiment. In accordance with the method, a stimulus may be applied to the cell through a device in a patch clamp system, and the characteristic of the cell may be measured with measurement circuitry while applying to the measurement circuitry i) a first compensation signal to compensate for a leakage resistance introduced by the patch clamp system and ii) a second compensation signal to compensate for a series resistance introduced by the device. The second compensation signal may be related to the measured characteristic of the cell and a third compensation signal that removes from the measured characteristic of the cell the effect thereon of the first compensation signal.

In various embodiments, the device that applies the stimulus to the cell is an electrode. The measured characteristic of the cell may be its current.

In general, in a further aspect, embodiments of the invention feature a system for compensating a series resistance of a device used in measuring a characteristic of at least one cell in an electrophysiological experiment. The system may include clamping circuitry configured to i) apply a stimulus to the cell through the device and ii) measure the characteristic of the cell. In addition, the system may include an operational amplifier having an output coupled to an input of the clamping circuitry. An input to an inverting terminal of the operational amplifier may be substantially equal to the output of the operational amplifier less a signal proportional to the measured characteristic of the cell.

In various embodiments, the device used in measuring the cell's characteristic is an electrode. Moreover, the measured characteristic of the cell may be its current.

In general, in another aspect, embodiments of the invention feature a subsystem for compensating for a capacitive waveform present in a patch clamp system. The subsystem may include measurement circuitry for measuring a magnitude of the capacitive waveform at each of a plurality of times and a plurality of compensation circuits. Each compensation circuit may have a unique time constant and be configured to output a gain-adjusted compensatory waveform to compensate for the capacitive waveform.

In general, in yet another aspect, embodiments of the invention feature a method of compensating for a capacitive waveform present in a patch clamp system. In accordance with the method, a magnitude of the capacitive waveform is measured at each of a plurality of times, and a gain-adjusted compensatory waveform is output form each of a plurality of compensation circuits to compensate for the capacitive waveform. Each compensation circuit may have a unique time constant.

In various embodiments, an unadjusted compensatory waveform is also output from each of the plurality of compensation circuits. The magnitude of each unadjusted compensatory waveform may be measured at each of the plurality of times. In addition, a gain adjustment may be calculated, by calculation circuitry, for each of the plurality of compensation circuits. Each gain adjustment may be calculated based on the measured magnitude of the capacitive waveform at each of the plurality of times and the measured magnitude of each unadjusted compensatory waveform at each of the plurality of times.

In one embodiment, calculation circuitry also calculates a leakage resistance present in the patch clamp system. In one such embodiment, the measurement of the capacitive waveform is adjusted to account for a virtual peak to be introduced into the capacitive waveform following compensation of the leakage resistance. The leakage resistance present in the patch clamp system may be compensated for and, while doing so, the magnitude of the capacitive waveform may be remeasured at each of the plurality of times.

These and other objects, along with advantages and features of the present invention, will become more apparent and may be better understood through reference to the following description, the accompanying drawings, and the claims. Furthermore, it is to be understood that the features of the various embodiments described herein are not mutually exclusive and may exist in various combinations and permutations.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 8 is a flow diagram of an illustrative embodiment of another method for compensating a patch clamp system;

FIG. 9 is a flow diagram of an illustrative embodiment of yet another method for compensating a patch clamp system;

FIG. 12 illustrates an equation for calculating a gain vector for use in the methods depicted in FIGS. 8 and 9;

DESCRIPTION

Described herein are various embodiments of subsystems and methods for use in patch clamp systems.

A. Overview

In broad overview, in accordance with embodiments of the invention, a subsystem and method are employed to compensate a larger patch clamp system that may be used in electrophysiological experiments. The subsystem may include compensation circuitry that is calibrated to compensate for non-idealities introduced by the patch clamp system. For example, the compensation circuitry may compensate for stray capacitance introduced by one or more components in the patch clamp system, leakage resistance present in the patch clamp system, and/or another non-ideality introduced by the patch clamp system. In one embodiment, the subsystem is configured to verify the compensation for the non-idealities introduced by the patch clamp system. As described in greater detail below, the subsystem may employ, for this purpose, model circuitry that models at least a portion of the patch clamp system.

In addition, as further described below, embodiments of the invention may be employed to determine a characteristic of a cell, such as its current, and a capacitance of a device that is used to hold the cell during an electrophysiological experiment. In one embodiment, the natural resting potential of the cell is measured and thereafter employed in determining the characteristic of the cell. In another embodiment, to determine the capacitance of the device used to hold the cell, a stimulus is applied to the device through a force amplifier and a response to the stimulus is measured using a separate sense amplifier. The response may then be analyzed, for example an RC time constant of the response may be calculated, and the device's capacitance determined therefrom.

In addition still, the patch clamp system described herein may employ an Rs compensation circuit that is capable of providing substantially full (i.e., 100%) compensation of the undesired series resistance Rs in a measuring electrode. Optionally, as described herein, leak current compensation may complement this Rs compensation without interfering with the Rs compensation.

B. Capacitance Compensation and Verification Thereof

Figure 3:
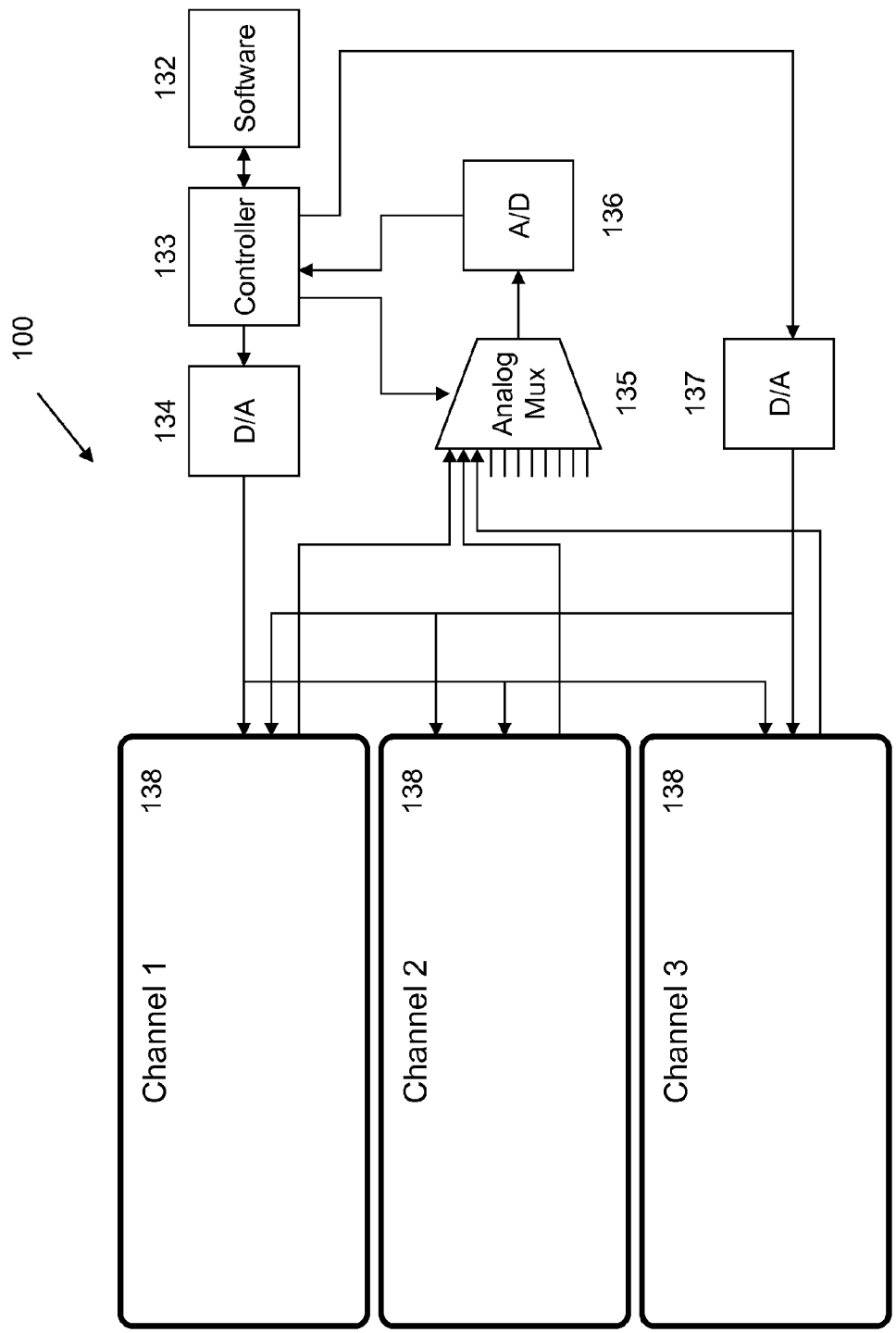
FIG. 3 is a circuit diagram of a patch clamp system in accordance with one embodiment of the invention.
Figure 4:
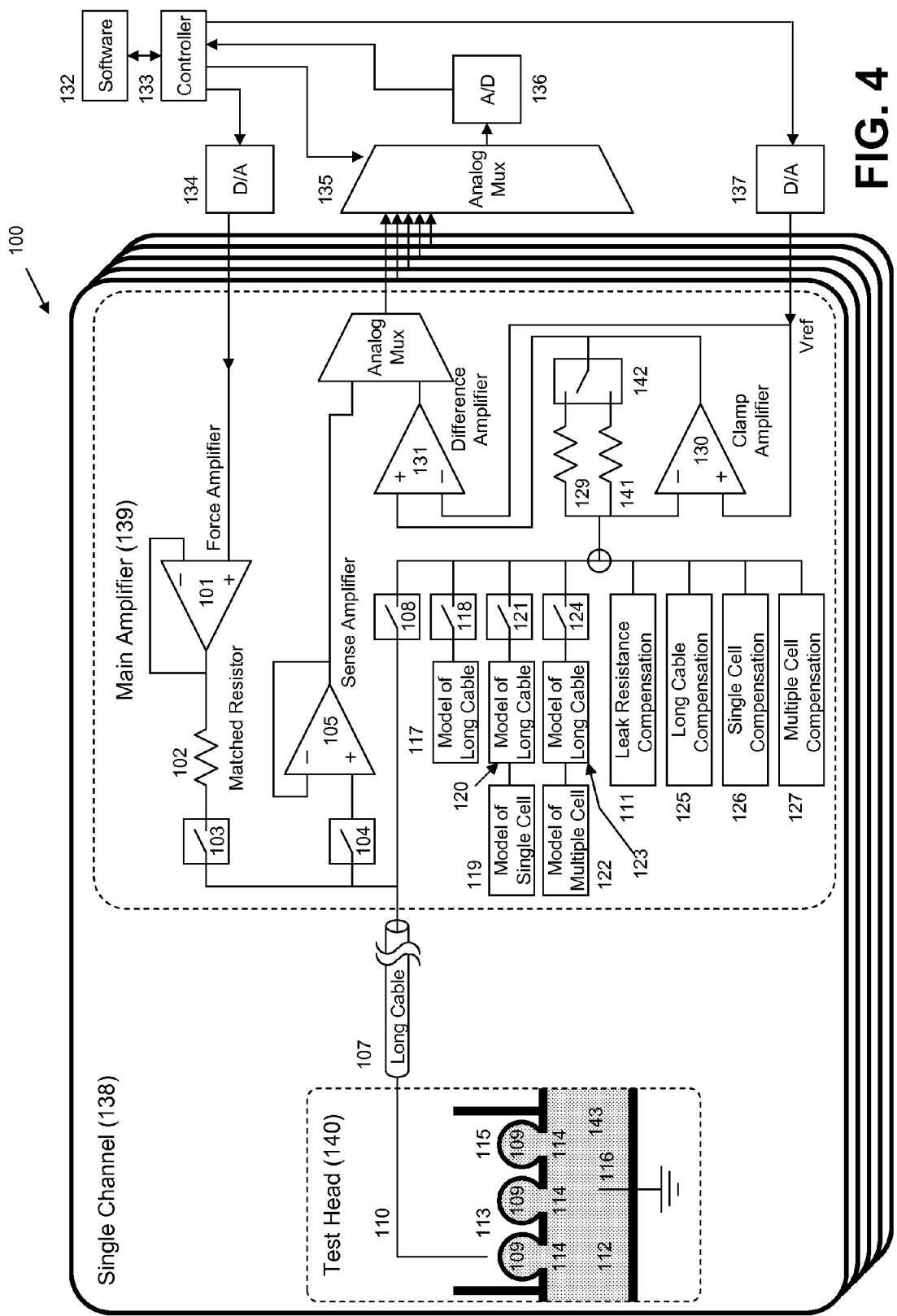
FIG. 4 is a circuit diagram of one embodiment of a single channel of the patch clamp system illustrated in FIG. 3.

FIG. 3 depicts an exemplary patch clamp system 100 having first, second, and third channels 138, although any number of channels 138 may be employed in the patch clamp system 100. FIG. 4 depicts one embodiment of a single channel 138 in greater detail. Each component in the single channel 138 may be an analog component. As illustrated in FIGS. 3 and 4, each channel 138 may provide output to software 132 through an analog multiplexer 135, analog-to-digital converter 136, and controller 133. In addition, software 132 may provide input to any channel 138 either through the controller 133 and digital-to-analog converter 134, or through the controller 133 and digital-to-analog converter 137. In addition, software 132 may control the analog multiplexer 135 through the controller 133.

In one embodiment, the software 132 is capable of instructing the controller 133 to control any or all components in each of the single channels 138. For example, the software 132 may instruct the controller 133 to open or close switches in the channels 138, to apply voltages to turn on/off certain components in the channels 138, and/or to sample the outputs of various components in the channels 138. Accordingly, even though it may not be explicitly stated as such, one of ordinary skill in the art will understand that when a component of a channel 138 is herein described to perform a given function, that component in fact performs that function in response to a command from the software 132 and controller 133. In one embodiment, software 132 interfaces with and employs computer memory (e.g., persistent and/or volatile storage) to store data and values, as described below.

In one embodiment, as illustrated in FIG. 4, each channel 138 of the patch clamp system 100 includes a test head 140, a main amplifier 139, and a long cable 107 therebetween. It should be understood that, as used throughout this description, the term "long cable" generally refers to a cable having a capacitance greater than or equal to approximately 30 pF. Thus, a 1-foot long 50 ohm coaxial cable having a capacitance of 30 pF/foot is a long cable, as are a 1.5-foot long 75 ohm coaxial cable having a capacitance of 20 pF/foot and a 2.5-foot long 93 ohm coaxial cable having a capacitance of 13 pF/foot.

Figure 1:
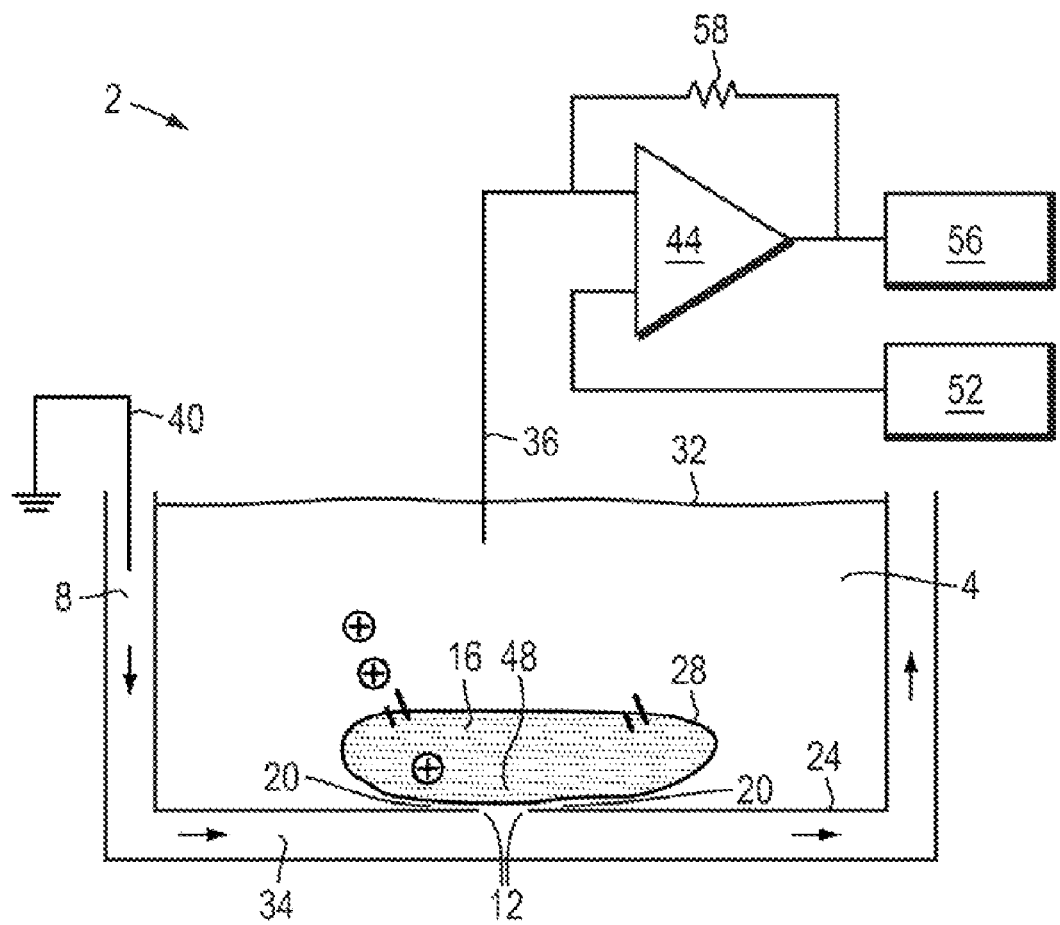
FIG. 1 is a schematic view of an exemplary planar patch clamp that is typically used in automated patch clamp systems.

As illustrated in FIG. 4, the test head 140 may include a holder device (or chip) 113 (i.e., a first chamber) in fluidic communication, through one or more holes 114 in a bottom surface thereof, with a second chamber 112. As described with reference to FIG. 1, one or more biological cells 109 may be deposited inside the first chamber 113 and drawn towards the hole(s) 109. A seal of high electrical resistance (e.g., in the range of several hundred MΩ to greater than 1 GΩ) may then be formed between the bottom surface of the first chamber 113 and the membrane(s) of the cell(s) 109. As illustrated, the first chamber 113 may be filled with an extracellular ionic solution 115 and the second chamber 112 filled with a saline buffer solution 143 that may contain a proper concentration of antibiotics. As described with reference to FIG. 1, the cell(s) 109 may be permeabilized (e.g., electrically, through negative pressure, or through the use of antibiotics) such that intracellular fluid from the cell(s) 109 mixes with the buffer solution 143. In one embodiment, a sensing electrode 110 is placed in contact with the extracellular ionic solution 115, and a bath electrode 116, connected to ground, is placed in contact with the buffer solution 143 (i.e., is effectively placed inside the cell(s) 109). As described further below, the sensing and bath electrodes 110, 116 may be used together with measurement circuitry (e.g., a voltage clamp amplifier 130, current-to-voltage gain resistors 129 and 141, and a difference amplifier 131) to measure a characteristic of the cell(s) 109, such as the current flowing through its/their membrane(s).

Figure 5:
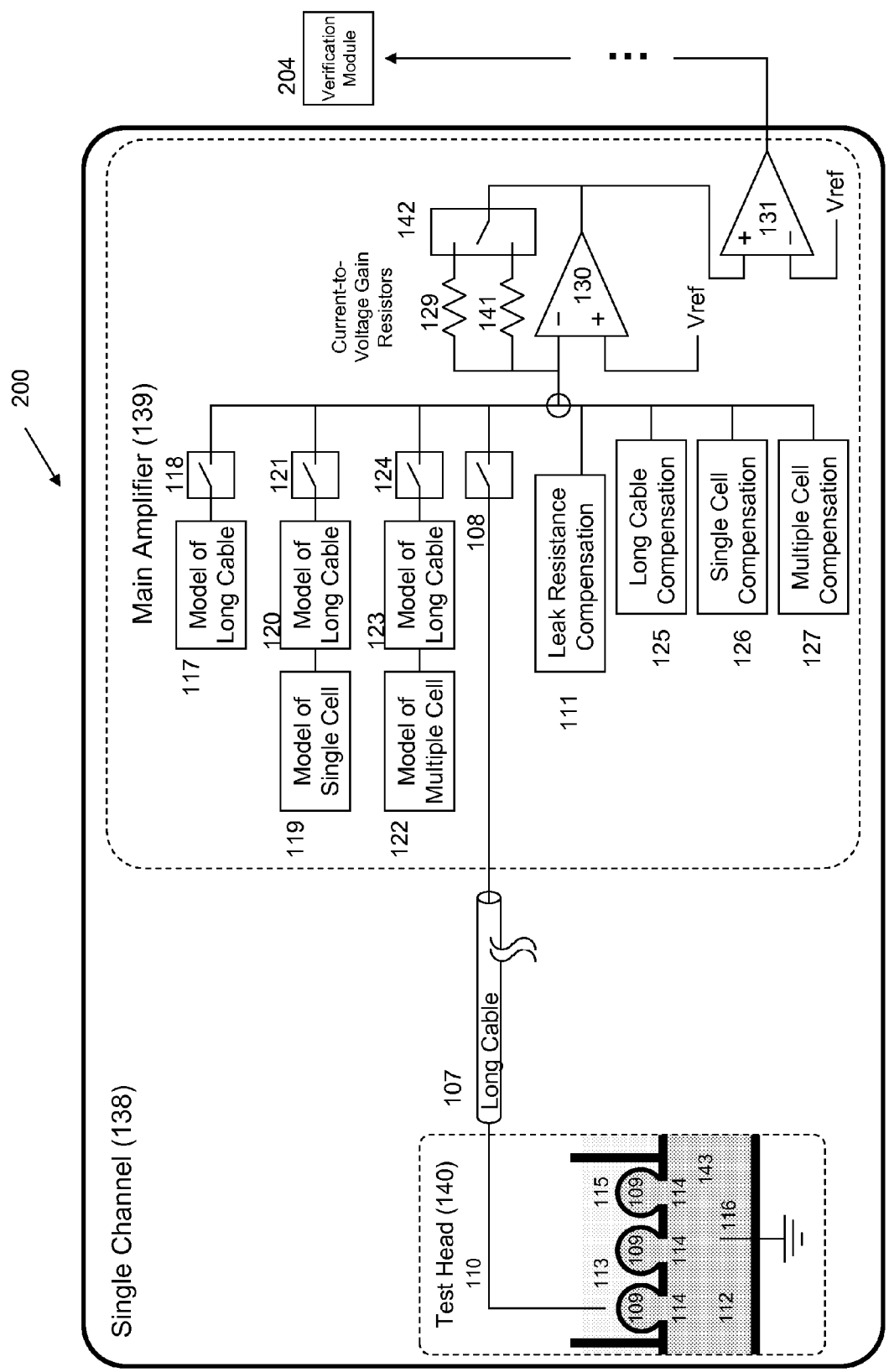
FIG. 5 is a circuit diagram of one embodiment of a subsystem of the patch clamp system illustrated in FIG. 3.

FIG. 5 depicts a subsystem 200 of the patch clamp system 100 depicted in FIGS. 3 and 4. With reference to FIGS. 4 and 5, in general, in one embodiment, the subsystem 200 is used to compensate for non-idealities present in, or introduced into, the patch clamp system 100 when it is used in electrophysiological experiments. For that purpose, the subsystem 200 may include, as illustrated, model circuitry (e.g., components 117, 119, 120, 122, and/or 123) that is configured to model at least a portion of the patch clamp system 100, and compensation circuitry (e.g., components 111, 125, 126, and/or 127) that is configured to compensate for the non-idealities.

In one embodiment, the model circuitry includes components 117, 120, and 123 to model the long cable 107 that connects the sensing electrode 110 located within the test head 140 to the main amplifier 139. In addition, the model circuitry may include a component 119 to model a single cell 109 positioned within the holder device (or chip) 113, and a component 122 to model multiple cells 109 positioned within the holder device (or chip) 113. When used together, components 119 and 120 model the long cable 107 in series with a single cell 109. Similarly, when used together, components 122 and 123 model the long cable 107 in series with multiple cells 109. Each component 117, 119, 120, 122, and 123 of the model circuitry may be implemented as any circuit or waveform generator that is capable of generating an analog signal as described below. For example, in one embodiment, the components 117, 120, and 123 each generate a capacitive spike modeling the capacitive spike to be introduced into the patch clamp system 100 by the long cable 107, the component 119 generates a capacitive spike modeling the capacitive spike to be introduced into the patch clamp system 100 by a single cell 109, and the component 122 generates a capacitive spike modeling the capacitive spike to be introduced into the patch clamp system 100 by multiple cells 109.

For its part, the compensation circuitry may include a component 125 that is configured to compensate for a stray capacitance introduced by the long cable 107 (and/or by a model 117, 120, 123 of the long cable 107), a component 126 that is configured to compensate for a stray capacitance introduced by a single cell 109 positioned within the holder device 113 (and/or by the model 119 of the single cell 109), and/or a component 127 that is configured to compensate for a stray capacitance introduced by multiple cells 109 positioned within the holder device 113 (and/or by the model 122 of the multiple cells 109). When used together, the components 125 and 126 may compensate for a stray capacitance introduced by the long cable 107 in series with a single cell 109 (and/or by the circuitry 119, 120 that models the long cable 107 in series with a single cell 109). Similarly, when used together, the components 125 and 127 may compensate for a stray capacitance introduced by the long cable 107 in series with multiple cells 109 (and/or by the circuitry 122, 123 that models the long cable 107 in series with multiple cells 109). Again, each component 125, 126, and 127 of the compensation circuitry may be implemented as any circuit or waveform generator that is capable of generating an analog signal as described below. For example, in one embodiment, the component 125 generates a capacitive spike of equal magnitude and time constant as, but opposite in polarity to, the capacitive spike generated by the long cable 107 (and/or generated by the model 117, 120, or 123 of the long cable 107), the component 126 generates a capacitive spike of equal magnitude and time constant as, but opposite in polarity to, the capacitive spike generated by a single cell 109 positioned within the holder device 113 (and/or generated by the model 119 of the single cell 109), and component 127 generates a capacitive spike of equal magnitude and time constant as, but opposite in polarity to, the capacitive spike generated by multiple cells 109 positioned within the holder device 113 (and/or generated by the model 122 of the multiple cells 109).

In addition, the compensation circuitry may include a component 111 that is configured to compensate for a leakage resistance introduced by the patch clamp system 100. As described further below, the various components 111, 125, 126, 127 of the compensation circuitry may be calibrated, at various times, with first calibration values to compensate for non-idealities (e.g., stray capacitances) introduced by the components 117, 119, 120, 122, 123 of the model circuitry. At other times, the various components 111, 125, 126, 127 of the compensation circuitry may be calibrated with second calibration values to compensate for non idealities (e.g., stray capacitances) introduced by the actual components (e.g., the long cable 107 and cell(s) 109) of the patch clamp system 100.

The subsystem 200 may also include the measurement circuitry (e.g., the voltage clamp amplifier 130, the current-to-voltage gain resistors 129 and 141, and the difference amplifier 131) that is configured to measure a characteristic of one or more biological cells 109 while, at the same time, receiving input from the compensation circuitry in order to compensate for non-idealities present in, or introduced into, the patch clamp system 100. In addition, the subsystem 200 may include a verification module 204. In one embodiment, the verification module 204 is implemented in software 132. Alternatively, the verification module 204 may be implemented in hardware, such as in an application specific integrated circuit (ASIC) or a field programmable gate array (FPGA). In still another embodiment, the verification module 204 may be one or more general-purpose microprocessors (e.g., any of the PENTIUM microprocessors supplied by Intel Corp.) programmed using any suitable programming language or languages (e.g., C++, C#, java, Visual Basic, LISP, BASIC, PERL, etc.).

As illustrated in FIGS. 4 and 5, the model circuitry, the compensation circuitry, and the measurement circuitry may all be advantageously located within the main amplifier system 139. Moreover, as illustrated in FIG. 4, ultra-low capacitance switches 103, 104, 108, 118, 121, 124, and 142 may be employed within the main amplifier 139. It should be understood that, as used throughout this description, the term "ultra low capacitance switch" generally refers to a switch having an "off" capacitance of less than approximately 3 pF. For example, each of the ultra-low capacitance switches 103, 104, 108, 118, 121, 124, and 142 may be implemented by an electromechanical relay, by a solid state relay (such as a PS7200R solid state relay manufactured by NEC Corporation of Tokyo, Japan), by a reed relay (such as a Pickering Series 103 reed relay manufactured by Pickering Electronics Limited of Clacton-on-Sea, Essex, England), by an RF/GRF series relay (e.g., an RF180 relay, a GRF172 relay, or a GRF342 relay) manufactured by Teledyne Relays, Inc. of Hawthorne, Calif., by an ADG1221, ADG1222, or ADG1223 switch manufactured by Analog Devices, Inc. of Norwood, Mass., by an SD5000, SD5001, SD5400, or SD5401 switch manufactured by Linear Integrated Systems, Inc. of Freemont, Calif., by a MAX326/327 switch manufactured by Maxim Integrated Products, Inc. of Sunnyvale, Calif., or by a photo-MOS switch (such as a TLP3116 switch manufactured by Toshiba Corporation of Tokyo, Japan).

In one embodiment, and with reference again to FIGS. 4 and 5, a resistor of greater than a few giga-ohms is used for one or more of the current-to-voltage gain resistors 129 and 141. Typically, such high value resistors do not have tight tolerances (e.g., the tolerances may be as great as 20%), which may result in gain error for the voltage clamp amplifier 130. Accordingly, in one embodiment of the invention, the actual resistances of the current-to-voltage gain resistors 129 and 141 are calculated. For example, the effective resistance (Reff) of the model circuitry 119, 120 (implemented, for example, through the use of tight tolerance (e.g., 1% or less) resistors in the model circuitry 119) may be known. Then, with switch 121 closed and switches 108, 118, and 124 open, a voltage (Vref) may be applied to the non-inverting input terminal of the voltage clamp amplifier 130. The actual resistance of the current-to-voltage gain resistor 129 or the current-to-voltage gain resistor 141 (depending on which one is connected by the switch 142 between the inverting input terminal and the output terminal of the voltage clamp amplifier 130) may then be calculated through a simple voltage divider equation by using the known effective resistance of the model circuitry 119, 120 (Reff), the voltage at the inverting input terminal of the voltage clamp amplifier 130 (i.e., Vref, as the input terminals of the voltage clamp amplifier 130 track each other in potential), and the observed voltage at the output terminal of the voltage clamp amplifier 130 (Vout). In other words, $$R_{129} = (Reff * Vout/Vref) - Reff$$

$$R_{141} = (Reff * Vout/Vref) - Reff$$

These actual resistance values for the current-to-voltage gain resistors 129, 141 may then be used to more accurately calculate the values and characteristics described herein, such as, for example, the current flowing through the membrane(s) of the cell(s) 109.

Figure 6:
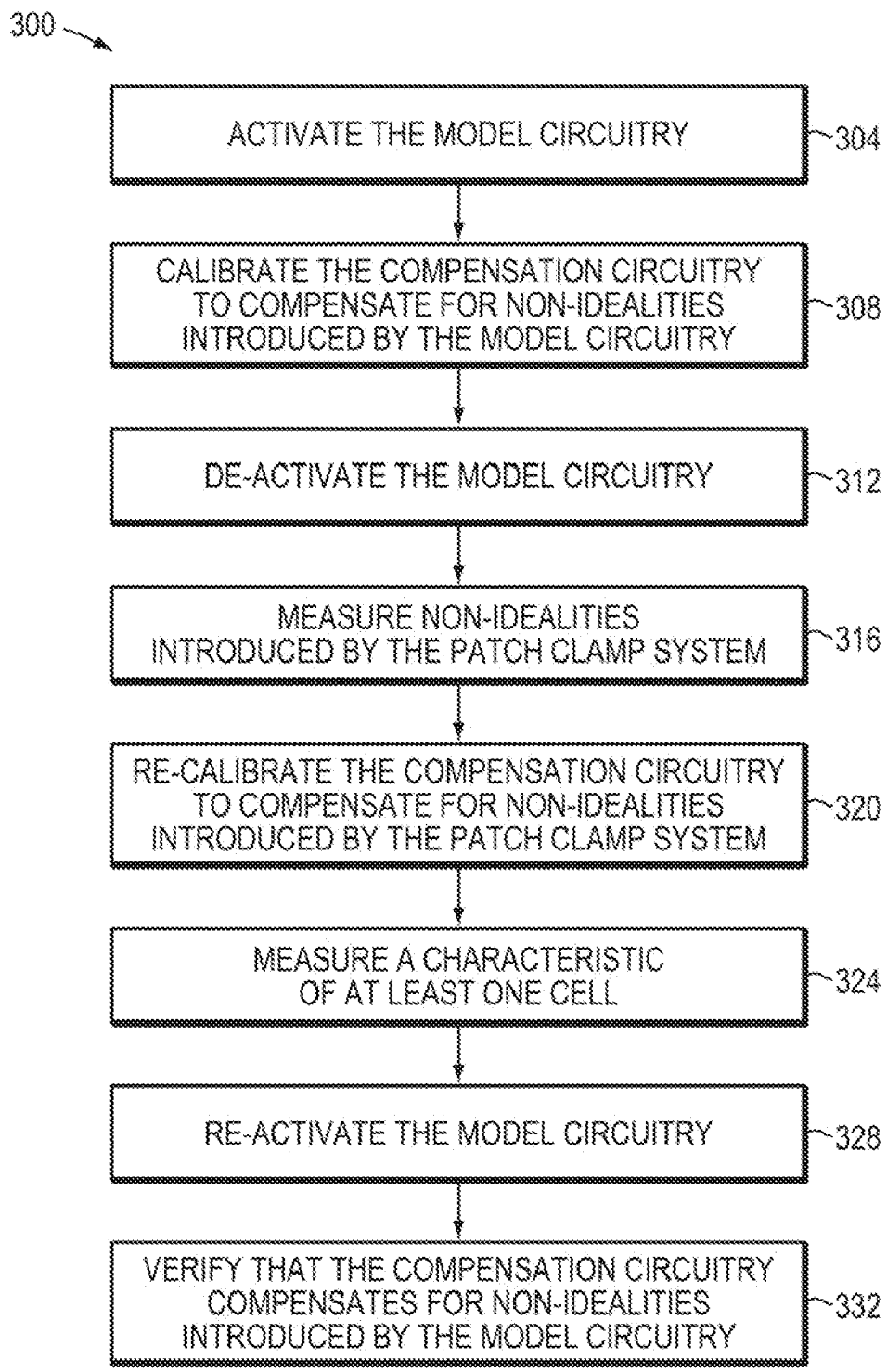
FIG. 6 is a flow diagram of an illustrative embodiment of a method for compensating a patch clamp system.

With reference now to FIG. 6, in one embodiment of a method 300 for compensating the patch clamp system 100 when it is used in electrophysiological experiments, the compensation circuitry is calibrated, at step 308, with at least one first calibration value to compensate for non-idealities introduced by the model circuitry, a characteristic of one or more cell(s) is measured at step 324, and, following the measuring of the characteristic, the compensation circuitry is tested, at step 332, to verify that it still compensates for non-idealities introduced by the model circuitry. Optionally, the method 300 may also include activating the model circuitry at step 304 prior to calibrating the compensation circuitry (at step 308) with the first calibration value(s), de-activating the model circuitry at step 312, measuring at step 316 non-idealities (e.g., stray capacitances) introduced by at least one component in the patch clamp system 100, and re-calibrating the compensation circuitry with at least one second calibration value at step 320 to compensate for non-idealities introduced by the patch clamp system 100. In addition, the method 300 may also optionally include re-activating the model circuitry at step 328 following the measuring of the characteristic of the one or more cell(s) 109 at step 324.

In greater detail, and with reference to FIGS. 4-6, the model circuitry is first activated at step 304 and the compensation circuitry is then calibrated, with at least one first calibration value, at step 308 to compensate for non-idealities introduced by the model circuitry. To activate the model circuitry at step 304, switch 108 may first be opened to disconnect the test head 140 from the main amplifier 139. One or more switches 118, 121, and 124 may then be closed to connect one or more of the model circuitry's components 117, 119, 120, 122, 123 to voltage clamp amplifier 130. At step 308, one or more of the compensation circuitry's components 125, 126, 127 may then be calibrated to compensate for non-idealities (e.g., stray capacitances) introduced by the model circuitry in question.

In one embodiment, steps 304 and 308 are iteratively repeated to independently calibrate each component 125, 126, 127 of the compensation circuitry. For example, switch 118 may first be closed at step 304 and then (with switches 121 and 124 open) the component 125 may be calibrated at step 308 with a first calibration value to compensate for a stray capacitance introduced by the model circuitry 117 of a long cable. More specifically, in one embodiment, when connected to the voltage clamp amplifier 139, the model circuitry 117 will generate a signal having a capacitive spike modeling the capacitive spike that will be introduced into the patch clamp system 100 by the long cable 107. Accordingly, the component 125 may be calibrated, with a first calibration value, to produce a capacitive spike substantially equal in magnitude and time constant, but opposite in polarity, to the capacitive spike generated by the model circuitry 117. For example, in one embodiment, the component 125 is configured to output, by default, a capacitive spike having default magnitude, time constant, polarity values. In such a case, the first calibration value applied to the component 125 may be a multiplying factor that causes the component 125 to output a capacitive spike substantially equal in magnitude and time constant, but opposite in polarity, to the capacitive spike generated by the model circuitry 117. As will be understood by one skilled in the art, because the model circuitries 117, 120, and 123 each output a signal having a capacitive spike that is substantially the same (i.e., a signal having a capacitive spike that is substantially the same as the capacitive spike that will be generated by the long cable 107), calibrating the component 125 to compensate for the capacitive spike generated by the model circuitry 117 also calibrates the component 125 to compensate for the capacitive spikes generated by the model circuitries 120 and 123.

Following calibration of component 125 at step 308, switch 118 may then be opened and switch 121 closed at step 304. The component 126 may then be calibrated at step 308 with a first calibration value to compensate for a stray capacitance introduced by the model circuitry 119 of a single cell. More specifically, in one embodiment, when connected to the voltage clamp amplifier 139, the model circuitry 119 will generate a signal having a capacitive spike modeling the capacitive spike that will be introduced into the patch clamp system 100 by a single cell 109 when it is positioned within the holder device 113, and model circuitry 120 will generate a signal having a capacitive spike modeling the capacitive spike that will be introduced into the patch clamp system 100 by the long cable 107. As described above, the component 125 has already been calibrated with a first calibration value to compensate for the capacitive spike introduced by the model circuitry 120 of the long cable 107. Accordingly, a first calibration value (e.g., a multiplying factor) may be applied to the component 126 in order to cause it to output a capacitive spike substantially equal in magnitude and time constant, but opposite in polarity, to the capacitive spike that will remain after the component 125 partially compensates for the capacitive spike generated by the model circuitries 119 and 120 together. Because the component 125 essentially compensates for the capacitive spike generated by the model circuitry 120 of the long cable 107, this is equivalent to calibrating the component 126 with a first calibration value that compensates for the capacitive spike generated by the model circuitry 119 of the single cell 109. In such a fashion, the components 125 and 126, when used together, may compensate for a stray capacitance introduced by the model circuitry 119, 120 of a long cable in series with a single cell 109.

Step 304 may then again be performed to open switch 121 and close switch 124. The component 127 may then be calibrated at step 308 with a first calibration value to compensate for a stray capacitance introduced by the model circuitry 122 of multiple cells 109. More specifically, in one embodiment, when connected to the voltage clamp amplifier 139, the model circuitry 122 will generate a signal having a capacitive spike modeling the capacitive spike that will be introduced into the patch clamp system 100 by multiple cells 109 when they are positioned within the holder device 113, and model circuitry 123 will generate a signal having a capacitive spike modeling the capacitive spike that will be introduced into the patch clamp system 100 by the long cable 107. As described above, the component 125 has already been calibrated with a first calibration value to compensate for the capacitive spike introduced by the model circuitry 123 of the long cable 107. Accordingly, a first calibration value (e.g., a multiplying factor) may be applied to the component 127 in order to cause it to output a capacitive spike substantially equal in magnitude and time constant, but opposite in polarity, to the capacitive spike that will remain after the component 125 partially compensates for the capacitive spike generated by the model circuitries 122 and 123 together. Because the component 125 essentially compensates for the capacitive spike generated by the model circuitry 123 of the long cable 107, this is equivalent to calibrating the component 127 with a first calibration value that compensates for the capacitive spike generated by the model circuitry 122 of the multiple cells 109. In such a fashion, the components 125 and 127, when used together, may compensate for a stray capacitance introduced by the model circuitry 122, 123 of a long cable in series with multiple cells 109.

At step 308, once the components 125, 126, and 127 of the compensation circuitry have been calibrated with their first calibration values, those first calibration values may be stored, for example in memory employed by software 132, for later use as described below.

Following the calibration, at step 308, of the compensation circuit's components 125, 126, and 127, and prior to measuring the characteristic of the one or more cells 109 with the measurement circuitry at step 324, the model circuitry may be de-activated at step 312. In one embodiment, the model circuitry is de-activated by opening all of the switches 118, 121, and 124.

At this point in the method 300, the switch 108 may be closed to reconnect the test head 140 to the main amplifier 139. Then, non-idealities (e.g., stray capacitances) introduced by the patch clamp system 100 may be measured at step 316 with the use of the measurement circuitry (i.e., the voltage clamp amplifier 130, the current-to-voltage gain resistors 129 and 141, and the difference amplifier 131), and, at step 320, one or more of the compensation circuitry's components 125, 126, and 127 may be re-calibrated with at least one second calibration value to compensate for the non-idealities (e.g., stray capacitances) introduced by the patch clamp system 100.

In one embodiment, steps 316 and 320 are iteratively repeated to independently re-calibrate one or more of the compensation circuitry's components 125, 126, and 127. For example, with solutions 115 and 143 present in the holder device 113, but prior to depositing a single cell 109, or multiple cells 109, therein, the measurement circuitry may be employed, at step 316, to measure the capacitive spike generated by the long cable 107 and the holder device 113 of the patch clamp system 100, which may effectively be considered to be the capacitive spike generated by the long cable 107. Alternatively, the long cable 107 may be left open (rather than connected to test head 140) and the measurement circuitry employed, at step 316, to measure the capacitive spike generated solely by the long cable 107 of the patch clamp system 100. In either case, and in a similar manner to that described above with reference to step 308, the component 125 may then be re-calibrated at step 320 with a second calibration value to compensate for the stray capacitance introduced by the long cable 107 in the patch clamp system 100. More specifically, a second multiplying factor may be applied to the component 125 in place of the first multiplying factor previously applied thereto in order to cause the component 125 to output a capacitive spike substantially equal in magnitude and time constant, but opposite in polarity, to the capacitive spike just measured at step 316.

If, at step 324, the characteristic of a single cell 109 is to be measured, then the single cell 109 may be appropriately positioned within the device holder 113 as previously described and step 316 may be repeated to measure the capacitive spike generated by the long cable 107 of the patch clamp system 100 in series with the single cell 109. Then, in a similar manner to that described above with reference to step 308, the component 126 may be re-calibrated at step 320 with a second calibration value to compensate for the stray capacitance introduced by the single cell 109. More specifically, a second multiplying factor may be applied to the component 126 in place of the first multiplying factor previously applied thereto in order to cause the component 126 to output a capacitive spike substantially equal in magnitude and time constant, but opposite in polarity, to the remaining portion of the capacitive spike just measured at step 316 after that measured capacitive spike is partially compensated by the component 125. In such a fashion, the components 125 and 126, when used together, may compensate for the stray capacitance introduced by the long cable 107 in series with the single cell 109.

Alternatively, if, at step 324, the characteristic of multiple cells 109 is to be measured, then the multiple cells 109 may be appropriately positioned within the device holder 113 as previously described and step 316 may be repeated to measure the capacitive spike generated by the long cable 107 of the patch clamp system 100 in series with the multiple cells 109. Then, in a similar manner to that described above with reference to step 308, the component 127 may be re-calibrated at step 320 with a second calibration value to compensate for the stray capacitance introduced by the multiple cells 109. More specifically, a second multiplying factor may be applied to the component 127 in place of the first multiplying factor previously applied thereto in order to cause the component 127 to output a capacitive spike substantially equal in magnitude and time constant, but opposite in polarity, to the remaining portion of the capacitive spike just measured at step 316 after that measured capacitive spike is partially compensated by the component 125. In such a fashion, the components 125 and 127, when used together, may compensate for the stray capacitance introduced by the long cable 107 in series with the multiple cells 109.

At step 316, once the capacitive spike(s) in question (e.g., the capacitive spike introduced by long cable 107, introduced by the long cable 107 in series with the single cell 109, and/or introduced by the long cable 107 in series with multiple cells 109) has/have been measured, those measured values may be stored, for example in memory employed by software 132, for later use as described below. In addition, at step 320, once the components 125, 126, and/or 127 of the compensation circuitry have been re-calibrated with their second calibration values, those second calibration values may also be stored, for example in memory employed by software 132, for later use as described below.

In addition, at step 320, component 111 of the compensation circuit may be calibrated to compensate for leakage resistance introduced by the patch clamp system 100. Leakage resistance may be introduced into the patch clamp system 100 by, for example, the membrane resistance of the cell(s) 109 and a seal resistance between the holder device (or chip) 113 and the cell(s) 109. Accordingly, the leakage resistance present in the patch clamp system 100 may be calculated by, for example, dividing a stimulus voltage applied across those elements at the test head 140 by the response current measured to be flowing therethrough. In one embodiment, the leakage resistance is then compensated by calibrating the effective resistance of the leakage resistance compensation circuitry 111 to substantially match the calculated leakage resistance and then applying to the leakage resistance compensation circuitry 111 a voltage substantially equal in magnitude, but opposite in sign, to the voltage applied at the test head 140.

Following the re-calibration of the compensation circuitry at step 320, the characteristic of the one or more cells 109 deposited in the cell holder 113 may be measured at step 324 with the measurement circuitry (i.e., with the voltage clamp amplifier 130, one of the current-to-voltage gain resistors 129 and 141, and the difference amplifier 131). In one embodiment, just prior to measuring the characteristic of the one or more cells 109 at step 324, the gain of the voltage clamp amplifier 130 is increased. For example, in one embodiment, the current-to-voltage gain resistor 129 has a lower resistance than the current-to-voltage gain resistor 141. In such a case, steps 304-320 of the method 300 may be performed with current-to-voltage gain resistor 129 connected between the inverting input and the output of the amplifier 130, while step 324 is performed with current-to-voltage gain resistor 141 connected between the inverting input and the output of the amplifier 130. Switching between the two current-to-voltage gain resistors 129, 141 may be achieved through the use of the ultra low capacitance switch 142.

In one embodiment, the measured characteristic is the current conducted through the membranes of the one or more cells 109, and such measurement occurs while the compensation circuitry is contemporaneously employed to compensate for the non-idealities introduced by the patch clamp system 100. In other words, with reference again to FIGS. 4 and 5, in addition to the measured signal from the test head 140 being applied to the voltage clamp amplifier 130, a signal from component 111 is applied to the amplifier 130 to compensate for the leakage resistance present in the patch clamp system 100, a signal from component 125 is applied to the amplifier 130 to compensate for the stray capacitance introduced into the patch clamp system 100 by the long cable 107, and (depending on whether the characteristic of either a single cell 109 or multiple cells 109 is being measured) either a signal from the component 126 is applied to the amplifier 130 to compensate from the stray capacitance introduced into the patch clamp system 100 by the single cell 109 or a signal from the component 127 is applied to the amplifier 130 to compensate from the stray capacitance introduced into the patch clamp system 100 by the multiple cells 109. Data obtained from measuring the characteristic of the one or more cells may then be recorded and stored, for example in memory employed by the software 132.

Following measurement of the cells' characteristic, switch 108 may again be opened to disconnect the test head 140 from the main amplifier 139 and the model circuitry may be re-activated. Re-activating the model circuitry may be accomplished by, for example, closing either switch 121 or switch 124. In one embodiment, where the characteristic of a single cell 109 is measured at step 324, the model circuitry is re-activated by closing switch 121 to connect the models 119, 120 of a long cable in series with a single cell to the voltage clamp amplifier 130. Alternatively, in another embodiment, where the characteristic of multiple cells 109 is measured at step 324, the model circuitry is re-activated by closing switch 124 to connect the models 122, 123 of a long cable in series with multiple cells to the voltage clamp amplifier 130.

At step 332, the verification module 204 may test the compensation circuitry to verify that it still compensates for non-idealities introduced into the patch clamp system 100 by the model circuitry. To do so, the compensation circuitry's components 125, 126, and/or 127 are, in one embodiment, first re-calibrated with their respective first calibration values that were determined at step 308 and stored in the memory employed by software 132. In the case where switch 121 was closed at step 328, components 125 and 126 of the compensation circuit are then employed to compensate the signal generated by the model circuitry. On the other hand, in the case where switch 124 was closed at step 328, components 125 and 127 of the compensation circuit are employed to compensate the signal generated by the model circuitry. The verification module 204 then analyzes the aggregate signal (i.e., the combined signals from the model circuitry and the compensation circuitry) that is measured by the measurement circuitry. If a capacitive spike is detected, the verification module 204 may determine that a disturbance, beyond the typical non-idealities expected and compensated for, occurred in the patch clamp system 100 while measuring the characteristic of the one or more cells at step 324 and is still present. In such a case, the data collected in measuring the characteristic of the cell(s) may be disregarded. If, on the other hand, the compensation circuitry still does compensate for non-idealities introduced by the model circuitry (e.g., no noticeable capacitive spikes exist in the signal measured by the measurement circuitry), that is a good indication that no disturbance was present in the patch clamp system 100 during the measuring of the characteristic of the one or more cells at step 324, other than the typical non-idealities which were compensated for by the compensation circuitry. In this latter case, the verification module 204 may determine the data measured at step 324 to be accurate.

In one embodiment, for each component 125, 126, and 127 of the compensation circuitry, the verification module 204 is also employed to compare the respective first and second calibration values applied thereto to verify that the compensation for the non-idealities introduced by the patch clamp system 100 is proper. This may occur at or following step 332 or, alternatively, at any point following the determination of the second calibration values at step 320. For example, if the first and second calibration values differ by more than a tolerable amount (which may be chosen to suit a particular application), a flag may be set to inform an operator of a possible disturbance in the patch clamp system beyond the typical non-idealities expected therein (and modeled by the model circuitry). Such a disturbance may be rectified before beginning, or continuing with, the electrophysiological experiment at step 324. If data has already been collected from the electrophysiological experiment or is in the process of being collected, a decision may be made to disregard such data, discontinue the measuring of the characteristic of the cell(s), rectify the disturbance, re-calibrate the compensation circuitry, and/or re-commence the electrophysiological experiment.

In another embodiment, the values of the various capacitive spikes generated by the model circuitry at step 304 may be compared by the verification module 204 to the values of the corresponding stray capacitances measured in the patch clamp system 100 at step 316. For example, the value of the capacitance used to model the long cable in the model circuitry 117 may be compared to the measured capacitance of the long cable 107. In one embodiment, where the ratio of those capacitances is dissimilar from the ratio of the first and second calibration values used in calibrating the corresponding component of the compensation circuitry (e.g., where the ratio of the value of the capacitance used to model the long cable in the model circuitry 117 to the measured capacitance of the long cable 107 is dissimilar from the ratio of the first calibration value to the second calibration value used in calibrating the long cable compensation circuitry 125) by more than a tolerable amount (which may be chosen to suit a particular application), a flag may again be set to inform an operator of a possible disturbance in the patch clamp system 100 beyond the typical non-idealities expected therein (and modeled by the model circuitry). This verification may be performed by the verification module 204 at or following step 332 or, alternatively, at any point following the determination of the second calibration values at step 320. Accordingly, such a disturbance may be rectified before beginning, or continuing with, the electrophysiological experiment at step 324. If data has already been collected from the electrophysiological experiment or is in the process of being collected, a decision may be made to disregard such data, discontinue the measuring of the characteristic of the cell(s), rectify the disturbance, re-calibrate the compensation circuitry, and/or re-commence the electrophysiological experiment.

C. Additional Systems and Methods for Capacitance Compensation

Figure 7:
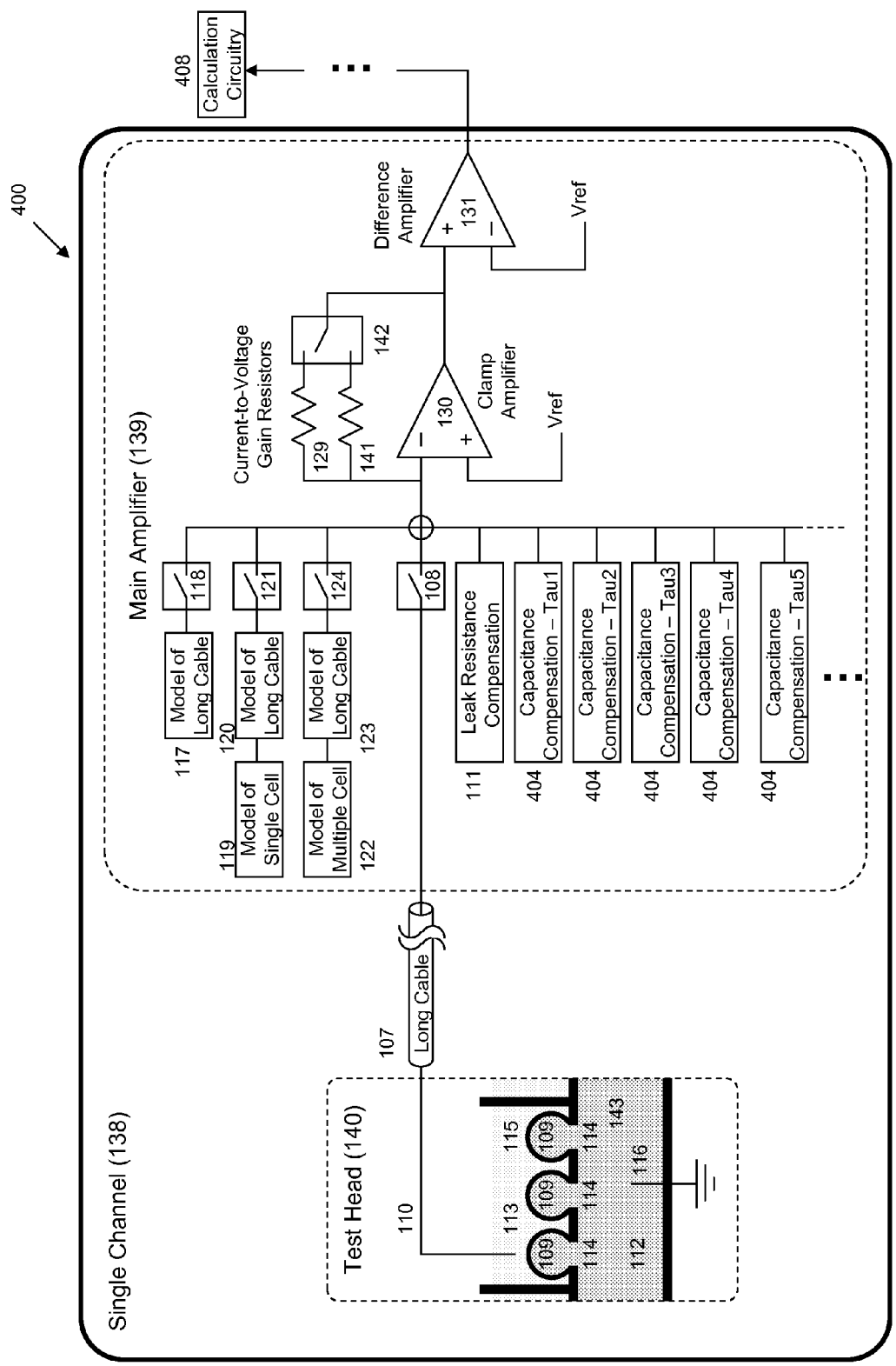
FIG. 7 is a circuit diagram of one embodiment of another subsystem of the patch clamp system illustrated in FIG. 3.

FIG. 7 depicts another embodiment of a subsystem 400 for compensating for a capacitive waveform present in the patch clamp system 100. The embodiment of the subsystem 400 illustrated in FIG. 7 includes all the same elements as the embodiment of the subsystem 200 illustrated in FIG. 5, except for the fact that the compensation circuitry of the two subsystems 200, 400 differs. More specifically, the individual components of the subsystem 200 that were configured to compensate for the capacitive spikes introduced by the long cable 107 (i.e., component 125), the single cell 109 (i.e., component 126), and the multiple cells 109 (i.e., component 127) are replaced in subsystem 400 by a plurality of different capacitance compensation circuits 404. In one embodiment of the invention, each of the plurality of capacitance compensation circuits 404 outputs a compensatory waveform to compensate for a capacitive spike present in the patch clamp system 100. Moreover, as described herein, each capacitance compensation circuit 404 may have a unique time constant. Like the subsystem 200, the subsystem 400 includes leakage resistance compensation circuitry 111 for compensating leakage resistance present in the patch clamp system 100, and measurement circuitry (e.g., voltage clamp amplifier 130, current-to-voltage gain resistors 129 and 141, and difference amplifier 131). In addition, like subsystem 200, the subsystem 400 is capable of compensating for both the capacitive spikes that originate in a single-cell configuration and the differing capacitive spikes that originate in a multiple-cell configuration.

As illustrated in FIG. 7, any number of capacitance compensation circuits 404 may be present in subsystem 400 of the patch clamp system 100. In addition, the methods 500, 600 detailed below may employ any number of the capacitance compensation circuits 404. To simplify discussion, however, the methods 500, 600 detailed below, and the associated algorithms/equations that they employ, will be described to use five capacitance compensation circuits 404.

The subsystem 400 of the patch clamp system 100 may also include calculation circuitry 408. The calculation circuitry 408 may be implemented as any software program (for example in software 132), hardware device, or combination thereof that is capable of achieving the functionality described herein. For example, the calculation circuitry 408 may be an application specific integrated circuit (ASIC) or a field programmable gate array (FPGA). Alternatively, the calculation circuitry 408 may be one or more general-purpose microprocessors (e.g., any of the PENTIUM microprocessors supplied by Intel Corp.) programmed using any suitable programming language or languages (e.g., C++, C#, java, Visual Basic, LISP, BASIC, PERL, etc.).

FIGS. 8 and 9 depict first and second exemplary methods 500, 600, respectively, of compensating for a capacitive spike present in the patch clamp system 100 using, for example, the subsystem 400. As previously mentioned, these methods 500, 600 are described as using five capacitance compensation circuits 404, although the methods 500, 600 may more generally use any number of capacitance compensation circuits 404.

Figure 10:
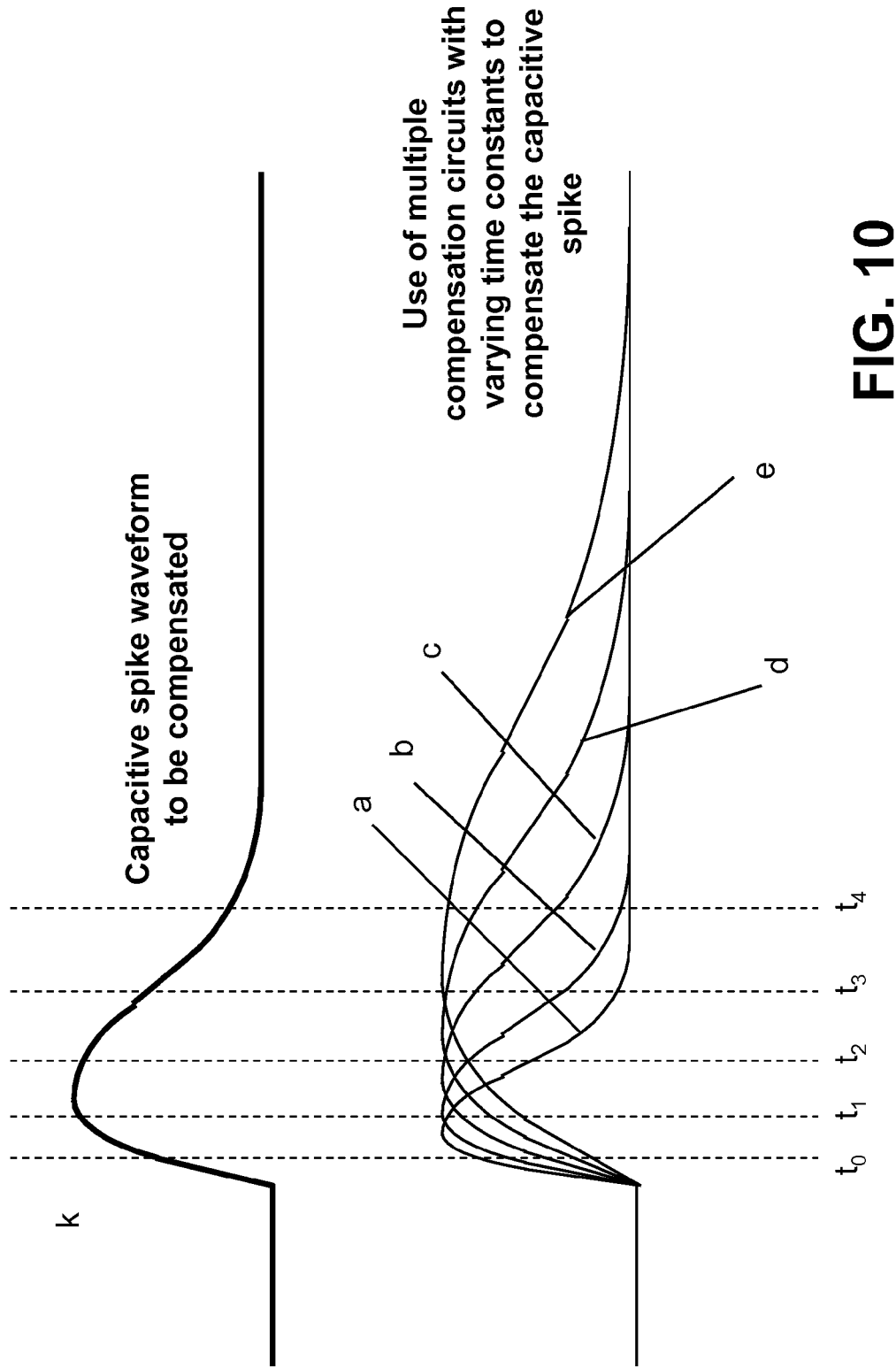
FIG. 10 illustrates a capacitive spike present in a patch clamp system and a plurality of unadjusted compensatory waveforms to be used in compensating the patch clamp system for that capacitive spike.

With reference first to method 500, at step 504 each of the five capacitance compensation circuits 404 are investigated. More specifically, each capacitance compensation circuit 404 may be stimulated to output an unadjusted compensatory waveform (e.g., a compensatory waveform having unity-gain). For example, with reference to FIG. 10, the first, second, third, fourth, and fifth capacitance compensation circuits 404 may be stimulated to output unadjusted compensatory waveforms "a," "b," "c," "d," and "e," respectively. As shown in FIG. 10, each of those unadjusted compensatory waveforms may have a unique time constant. As also shown in FIG. 10, the magnitude of each unadjusted compensatory waveform may then be measured by the measurement circuitry of the subsystem 400 at, for example, times $t_0$, $t_1$, $t_2$, $t_3$, and $t_4$.

At step 508 of the method 500, and with the five compensation circuits 404 turned off (e.g., disconnected from the voltage clamp amplifier 130 of the subsystem 400), the measurement circuitry of the subsystem 400 may measure the capacitive spike present in the patch clamp system 100 that is to be compensated for. More specifically, as illustrated in FIG. 10, the measurement circuitry of the subsystem 400 may also be used to measure the magnitude of the capacitive spike at, for example, times $t_0$, $t_1$, $t_2$, $t_3$, and $t_4$.

At step 512 of the method 500, the calculation circuitry 408 may calculate the leakage resistance present in the patch clamp system 100. As previously described, leakage resistance may be introduced into the patch clamp system 100 by, for example, the membrane resistance of the cell(s) 109 and a seal resistance between the holder device (or chip) 113 and the cell(s) 109. Accordingly, the calculation circuitry 408 may calculate the leakage resistance present in the patch clamp system 100 by, for example, dividing a stimulus voltage applied across those elements at the test head 140 by the response current measured to be flowing therethrough.

Figure 11:
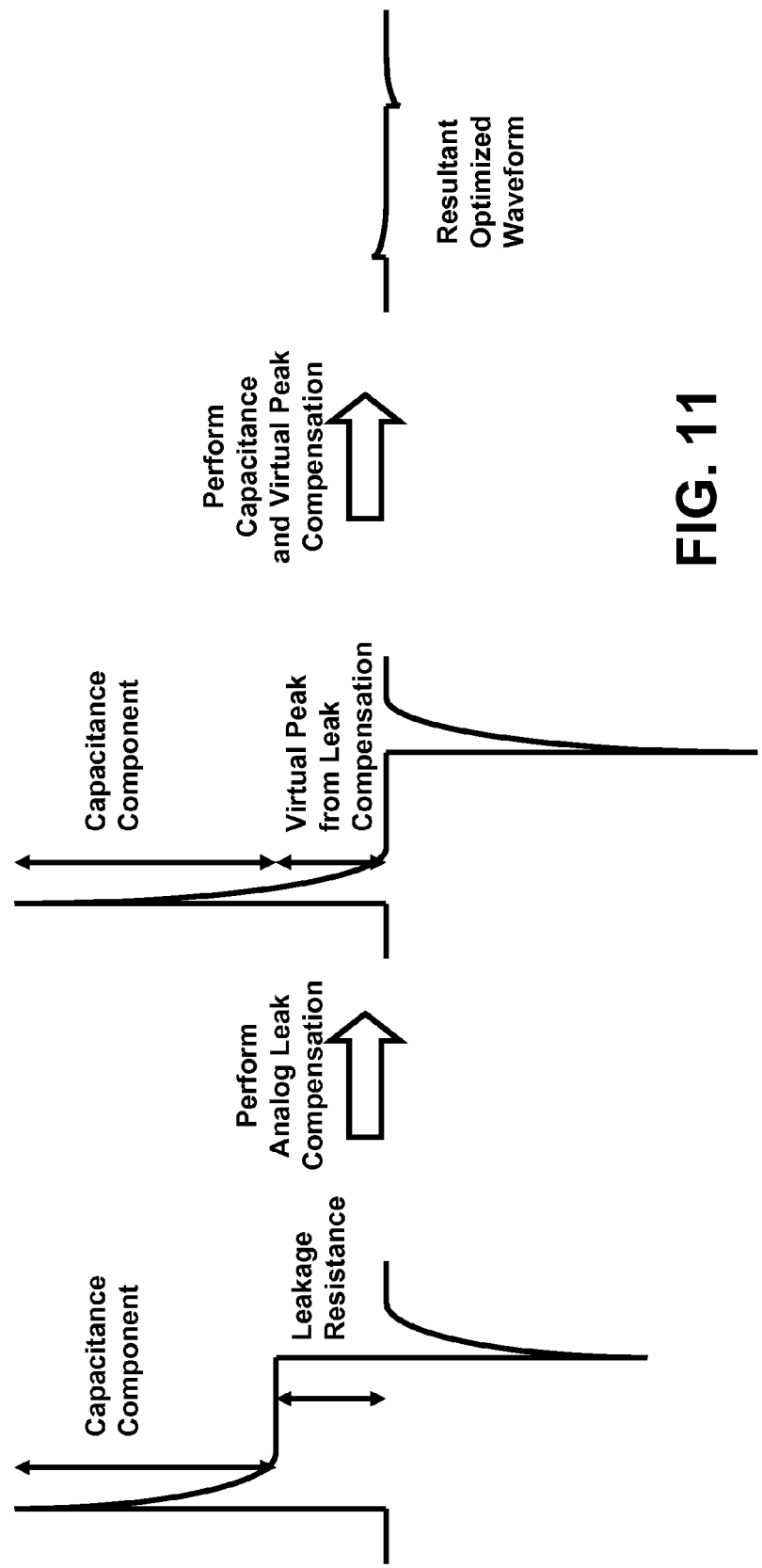
FIG. 11 illustrates a virtual peak that results in a capacitive spike following the compensation for leakage resistance in a patch clamp system.

Following calculation of the leakage resistance at step 512, the calculation circuitry 408 may, at step 516, adjust the measurements of the capacitive spike made at step 508 to account for a virtual peak that will be introduced into the capacitive spike at a later point in time when the leakage resistance in the patch clamp system 100 is compensated for. More specifically, as illustrated in FIG. 11, non-idealities present in the patch clamp system 100 introduce into the patch clamp system 100 a non-ideal waveform that includes two components: i) a component owing to stray capacitance present in the patch clamp system 100; and ii) a component owing to leakage resistance present in the patch clamp system 100. As also illustrated in FIG. 11, it has been observed that following compensation of the leakage resistance present in the patch clamp system 100, the capacitive spike is modified to reflect a virtual peak introduced from the effects of compensating the leakage resistance. In one embodiment, leakage resistance is compensated by setting the effective resistance of the leakage resistance compensation circuitry 111 to substantially match the calculated leakage resistance and then applying to the leakage resistance compensation circuitry 111 a voltage substantially equal in magnitude, but opposite in sign, to the voltage applied at the test head 140. Accordingly, the calculation circuitry 408 may adjust the measurements of the capacitive spike made at step 508 to account for the eventual effect that this leakage resistance compensation will have on the capacitive spike when the leakage resistance is in fact compensated for. More specifically, the calculation circuitry 408 may add an estimated leakage resistance compensation waveform to the capacitive spike waveform measured at step 508.

At step 520, the calculation circuitry 408 may calculate a gain adjustment for each of the five capacitance compensation circuits 404. More specifically, with reference to FIG. 12, a "Matrix M" may be populated with the magnitudes of each unadjusted compensatory waveform "a," "b," "c," "d," and "e" measured in step 504 at, for example, times $t_0$, $t_1$, $t_2$, $t_3$, and $t_4$. In addition, a "k vector" may be populated with the magnitudes of the capacitive spike measured in step 508 at times $t_0$, $t_1$, $t_2$, $t_3$, and $t_4$ with adjustments (determined at step 516) for the effect on the capacitive spike that will result when the leakage resistance of the patch clamp system 100 is compensated for. In other words, the "k vector" may be populated with the magnitudes of the capacitive spike measured in step 508 at times $t_0$, $t_1$, $t_2$, $t_3$, and $t_4$, plus the values of the estimated leakage resistance compensation waveform at those times $t_0$, $t_1$, $t_2$, $t_3$, and $t_4$. The gain adjustments to be applied to the five compensation circuits (i.e., gains $g_a$, $g_b$, $g_c$, $g_d$, and $g_e$ of the "g vector") may then be readily calculated.

Also at step 520 of the method 500, the calculated gains $g_a$, $g_b$, $g_c$, $g_d$, and $g_e$ may be applied to the five capacitance compensation circuits 404 that, at step 504, outputted the unadjusted compensatory waveforms "a," "b," "c," "d," and "e," respectively. The non-ideal leakage resistance and capacitive spike present in the patch clamp system 100 may then be compensated for. More specifically, with reference again to FIG. 7, the leakage resistance compensation circuitry 111 may output a waveform to compensate for the leakage resistance present in the patch clamp system 100 and the five capacitance compensation circuits 404 may each output a gain-adjusted compensatory waveform to compensate for the capacitive spike present in the patch clamp system 100.

As illustrated in FIG. 8, the method 500 may iterate through steps 508, 512, 516, and 520 any number of times, as desired, until the capacitive spike and leakage resistance are adequately compensated for. In other words, after a single pass through the steps 508, 512, 516, and 520 of the method 500, a small capacitive spike and/or component owing to the leakage resistance of the patch clamp system 100 may still be present (e.g., due to the calculated gains $g_a$, $g_b$, $g_c$, $g_d$, and $g_e$ for the capacitance compensation circuits 404 deviating slightly from the actual gains required to eliminate the capacitive spike). In one embodiment, further iteration through steps 508, 512, 516, and 520 leads to calculated gains $g_a$, $g_b$, $g_c$, $g_d$, and $g_e$ that more closely approximate the actual gains required to eliminate the capacitive spike.

Referring now to the method 600 depicted in FIG. 9, steps 604, 608, and 612 may be implemented in the same manner as described above for steps 504, 508, and 512, respectively, of the method 500. At step 616, the leakage resistance compensation circuitry 111 of the subsystem 400 may output a waveform to compensate for the leakage resistance present in the patch clamp system 100. At substantially the same time, and with the five compensation circuits 404 turned off (e.g., disconnected from the voltage clamp amplifier 130 of the subsystem 400), the measurement circuitry of the subsystem 400 may re-measure, at step 620, the capacitive spike present in the patch clamp system 100. As described with reference to step 508 of method 500 and as illustrated in FIG. 10, the measurement circuitry may specifically re-measure the magnitude of the capacitive spike at, for example, times $t_0$, $t_1$, $t_2$, $t_3$, and $t_4$. Those re-measured magnitude values may then be used by the calculation circuitry, at step 624, to populate the "k vector" illustrated in FIG. 12. The gain adjustments $g_a$, $g_b$, $g_c$, $g_d$, and $g_e$ to be applied to the five capacitance compensation circuits 404 may then be readily calculated, applied to the five compensation circuits 404, and the capacitive spike present in the patch clamp system 100 compensated for by outputting a gain-adjusted compensatory waveform from each of the five compensation circuits 404, as described above for the step 520 of the method 500.

Again, in a similar manner as described for the method 500, the method 600 may iterate through steps 608, 612, 616, 620 and 624 any number of times, as desired, until the capacitive spike and leakage resistance present in the patch clamp system 100 are adequately compensated for.

In one embodiment, performing steps 616 and 620 of the method 600 leads to a more accurate "k vector" than the "k vector" determined in step 516 of the method 500, as the values for the "k vector" of the method 600 are directly measured while the leakage resistance is compensated for. In contrast, the values for the "k vector" of the method 500 are predicted, based upon the effect that compensating the leakage resistance is anticipated to have on the capacitive spike. On the other hand, performing the method 500 is generally faster than performing the method 600, as the capacitive spike need not be twice generated and measured in the method 500. Accordingly, either method 500 or 600 may be implemented and used in the patch clamp system 100, depending on the particular application and the need for speed or accuracy in compensating for the capacitive spike present in the patch clamp system 100.

It will be understood by one skilled in the art that various modifications and/or additions may be made to either the method 500 or the method 600. For example, after the capacitive spike is measured at step 508 of the method 500 (or at step 608 of the method 600), it may be determined which two unadjusted compensatory waveforms output at step 504 (or at step 604) by the five capacitive compensation circuits 404 most closely resemble the capacitive spike. Then, the remaining steps of the method 500 (or of the method 600) may be narrowed to determine only the gain adjustment that is needed to be applied to the two capacitive compensation circuits 404 outputting those two waveforms, and, in one embodiment, only those two capacitive compensation circuits 404 need then be used in order to compensate for the capacitive spike. Eliminating consideration of the other three capacitive compensation circuits again speeds the completion of the method 500 (or the method 600).

D. Determining the Capacitance of the Holder Device

Figure 13:
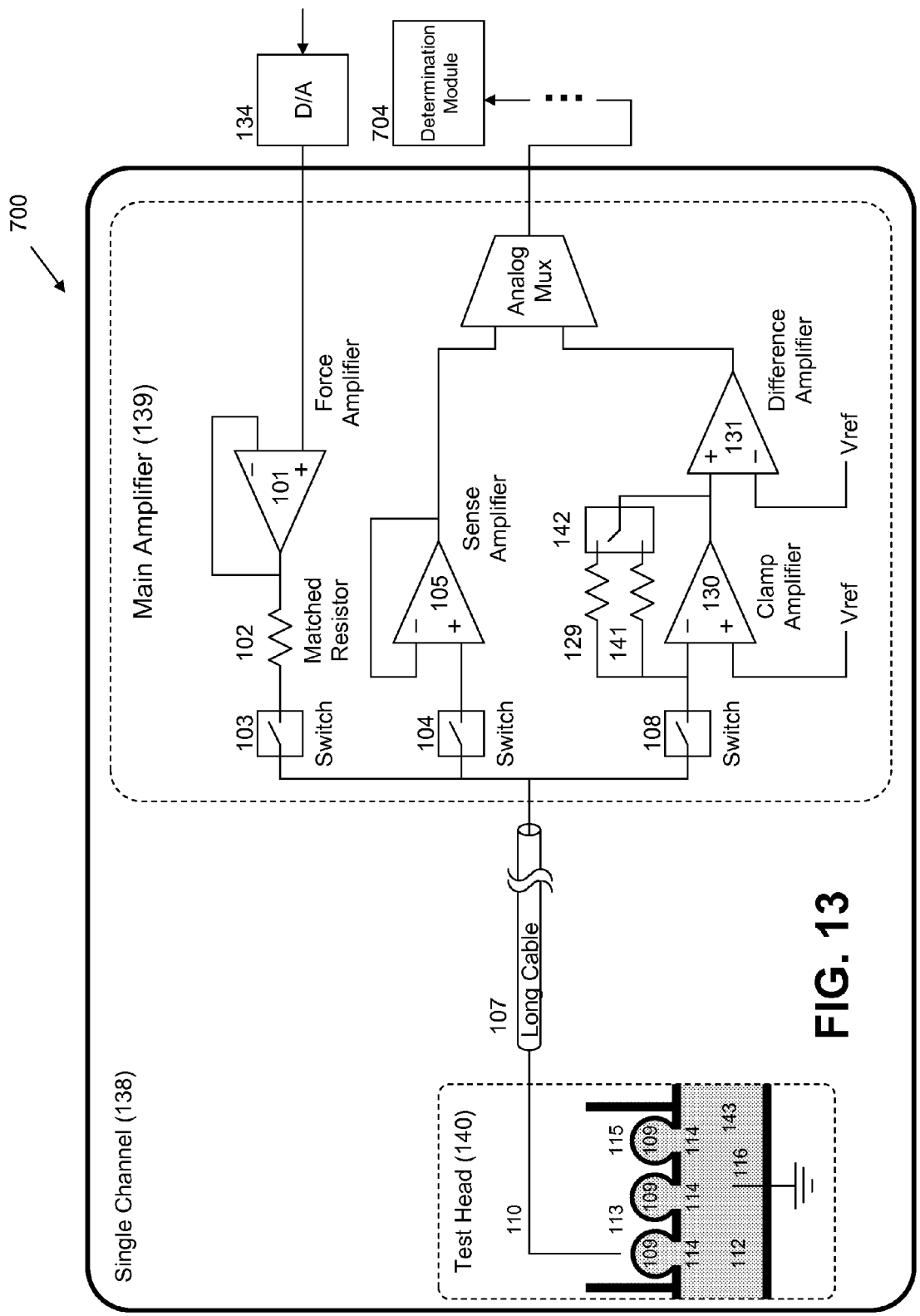
FIG. 13 is a circuit diagram of one embodiment of yet another subsystem of the patch clamp system illustrated in FIG. 3.
Figure 14A:
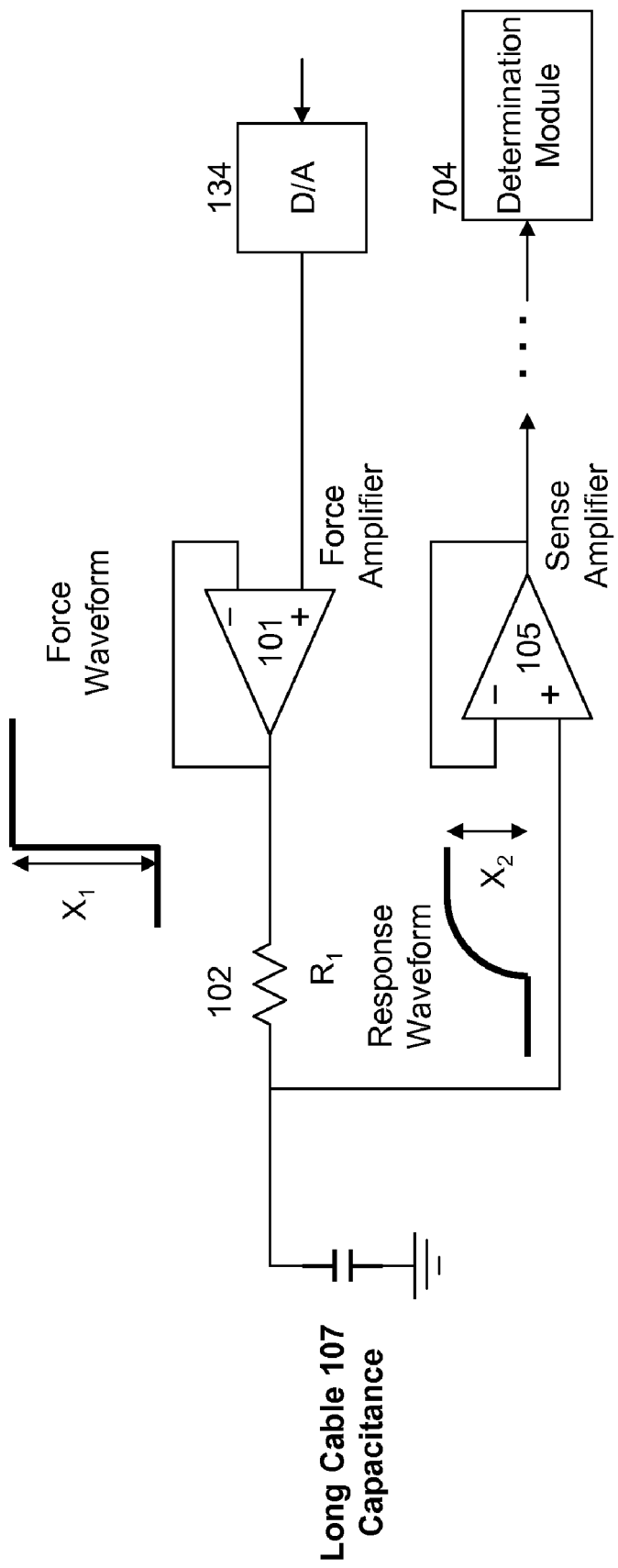
FIGS. 14A and 14B are each a partial circuit diagram of the subsystem depicted in FIG. 13 and are used to explain how the capacitance of a holder device (or chip) may be calculated.

FIG. 13 depicts a subsystem 700 of the patch clamp system 100 depicted in FIGS. 3 and 4. With reference to FIGS. 4 and 13, in general, in one embodiment, the subsystem 700 is employed to determine a capacitance of the holder device (or chip) 113 used to hold one or more cells 109 in an electrophysiological experiment. As illustrated, the subsystem 700 includes a force amplifier 101, a matched resistor 102 of known value, a separate sense amplifier 105, and a determination module 704, which may be implemented in software, such as in software 132, or in hardware, such as in an ASIC or an FPGA. In operation, switch 108 is first opened to disconnect the voltage clamp amplifier 130 from the test head 140, switches 103 and 104 are closed, and the long cable 107 is disconnected from the test head 140 and connected to ground. Then, as depicted in FIG. 14A, a stimulus (e.g., force waveform) of magnitude $X_1$ is applied to the long cable 107 through the force amplifier 101 and the matched resistor 102, a response to the stimulus is measured with the separate sense amplifier 105, and the determination module 704 calculates a first RC time constant ($\tau_1$) for the response to the stimulus (e.g., by measuring the approximate time taken for the response waveform to rise from zero volts to its full magnitude $X_2$). The first RC time constant ($\tau_1$) may then be stored in memory by the determination module 704.

Figure 14B:
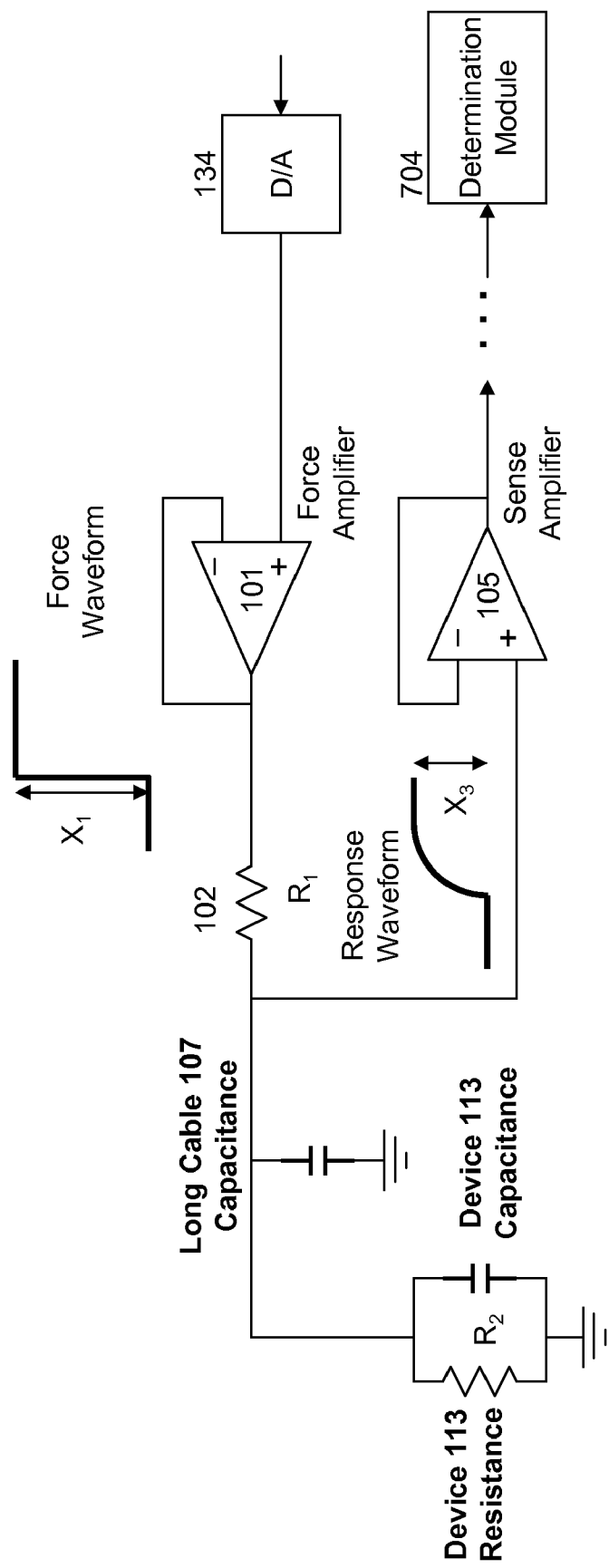

Then, as depicted in FIG. 14B, the long cable 107 is reconnected to test head 140, the same stimulus (e.g., force waveform) as before (i.e., having magnitude $X_1$) is applied to the holder device (or chip) 113 (without one or more cells 109 deposited therein) through the force amplifier 101, a response to the stimulus is measured with the separate sense amplifier 105, and the capacitance of the device 113 is determined by the determination module 704 by analyzing the response to the stimulus. For example, the determination module 704 may calculate a second RC time constant ($\tau_2$) for the response to the stimulus (e.g., by measuring the approximate time taken for the response waveform to rise from zero volts to its full magnitude $X_3$) and derive the capacitance of the device 113 therefrom. More specifically, with reference to FIG. 14B, the resistance $R_1$ of the matched resistor 102 is known, as is the magnitude $X_1$ of the applied stimulus. The full magnitude $X_3$ of the response to the stimulus is measured by the sense amplifier 105. Accordingly, the resistance $R_2$ of the device 113 may be readily determined by the determination module 704 from the voltage divider that the device 113 forms with the matched resistor 102:

$$R_2 = R_1 * X_3 / (X_1 - X_3)$$

Moreover, having calculated the first and second RC time constants ($\tau_1$ and $\tau_2$) of the responses to the stimulus, the determination module 704 may determine the capacitance of the device 113 as follows:

$$\text{Device 113 Capacitance} = (\tau_2 * (R_1 + R_2)/(R_1 * R_2)) - \tau_1 / R_1$$

As will be understood by one skilled in the art, having calculated the capacitance of the device 113, a component may be added to the compensation circuitry of the patch clamp system 100 to compensate for the capacitance of the device 113, thereby leading to a more accurate measurement of the cell's characteristic, as described below.

E. Measuring the Characteristic of the Cell(s)

Figure 15:
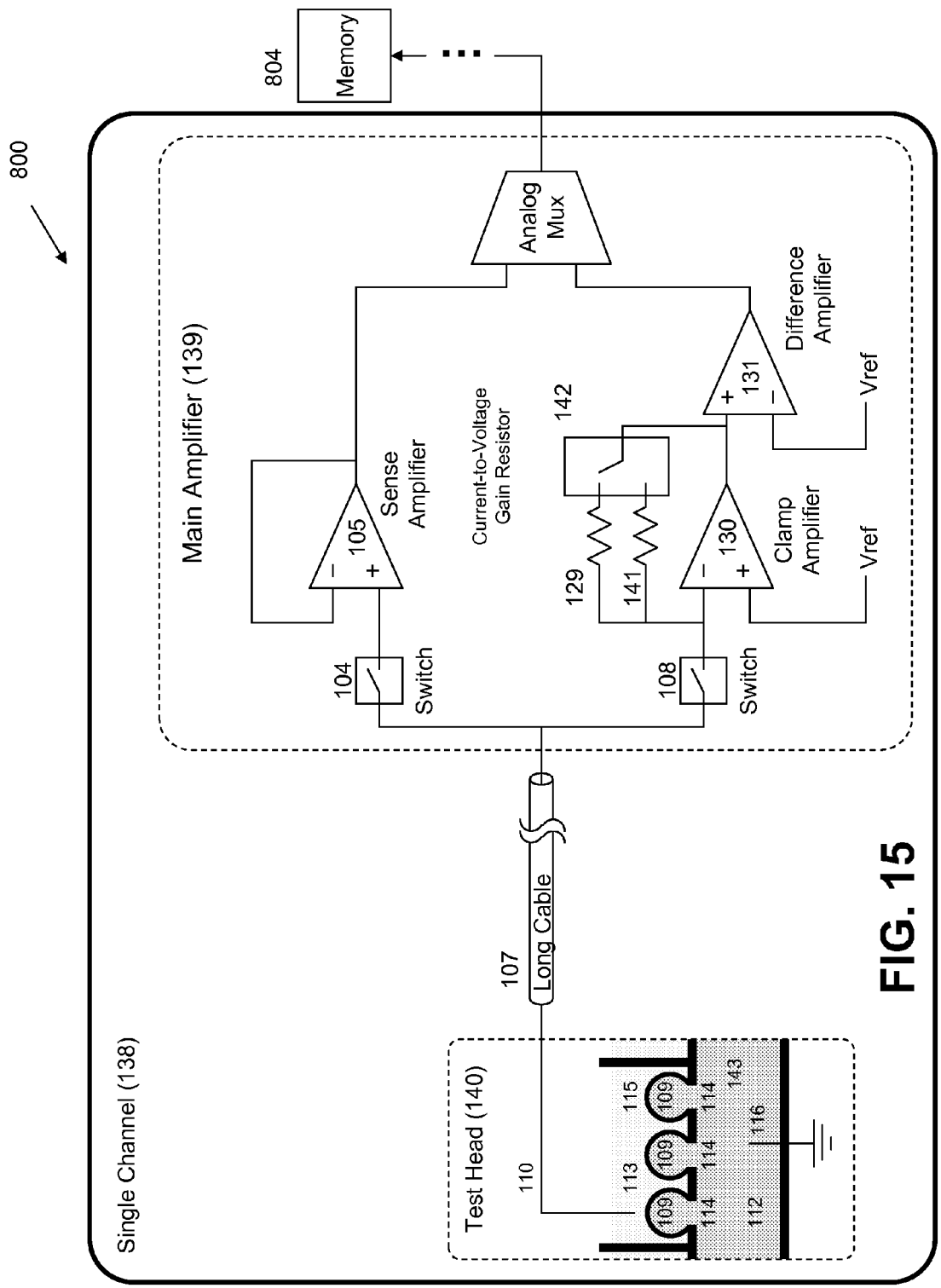
FIG. 15 is a circuit diagram of one embodiment of still another subsystem of the patch clamp system illustrated in FIG. 3.

FIG. 15 depicts a subsystem 800 of the patch clamp system 100 depicted in FIGS. 3 and 4. With reference to FIGS. 4 and 15, in general, in one embodiment, the subsystem 800 is employed to determine a characteristic of one or more cells 109. As illustrated, the subsystem 800 may include sensing circuitry (e.g., sense amplifier 105) configured to measure a natural resting potential of a cell 109, a memory 804 (for example in hardware and accessible by the software 132) configured to store the measured natural resting potential of the cell 109, and clamping circuitry (e.g., voltage clamp amplifier 130, current-to-voltage gain resistors 129 and 141, and difference amplifier 131).

Figure 16:
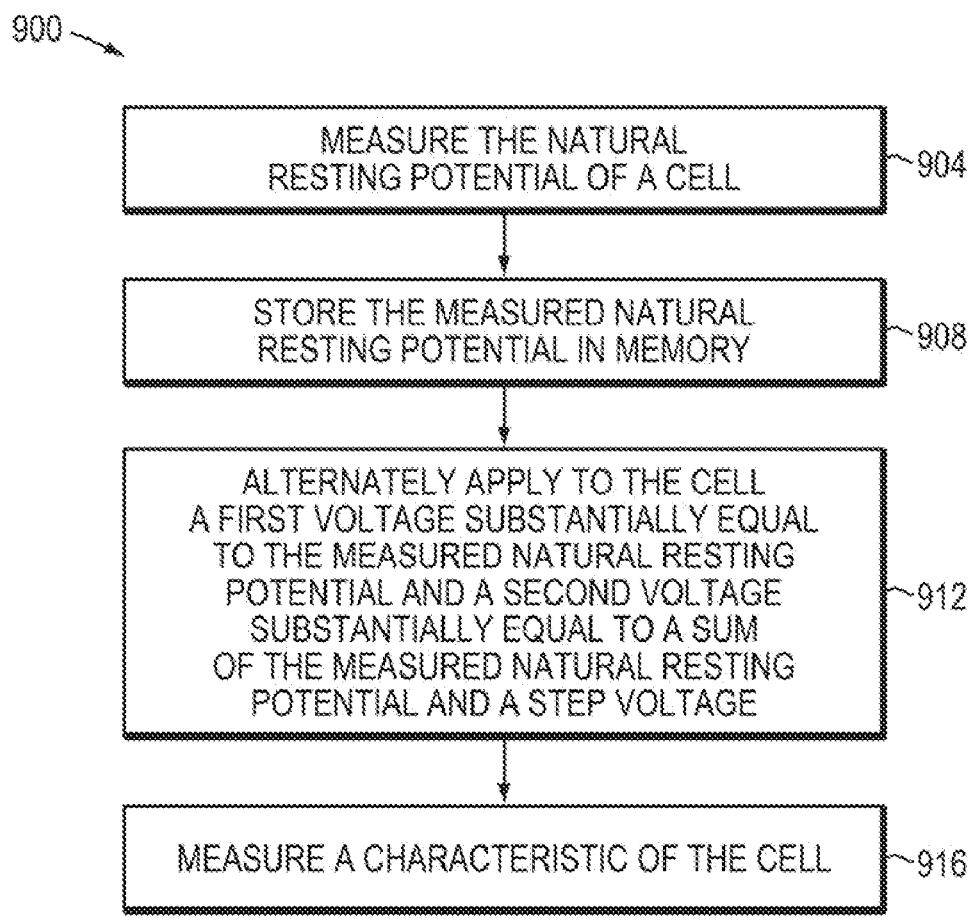
FIG. 16 is a flow diagram of an illustrative embodiment of a method for determining a characteristic of a cell.

FIG. 16 depicts one embodiment of a method 900 for determining a characteristic of the cell 109. At step 904, the natural resting potential of the cell 109 is measured. To do so, switch 108 is first opened to disconnect the voltage clamp amplifier 130 from the test head 140, and switch 104 is closed to connect the sense amplifier 105 to the test head 140. The natural resting potential of the cell 109 deposited within the holder device (or chip) 113 of the test head 140 may then be measured through the sense amplifier 105. The natural resting potential of a cell 109, as will be understood by one skilled in the art, is its membrane potential that would be maintained if there were no action potentials, synaptic potentials, or other active changes in its membrane potential. The natural resting potential is generally determined by the concentrations of the ions in the solutions 115, 143 on both sides of the cell 109 membrane and the ion transport proteins that are in the cell 109 membrane. Once the measured natural resting potential of the cell 109 is measured at step 904, it may be stored at step 908 in the memory 804 of the subsystem 800.

Figure 17:
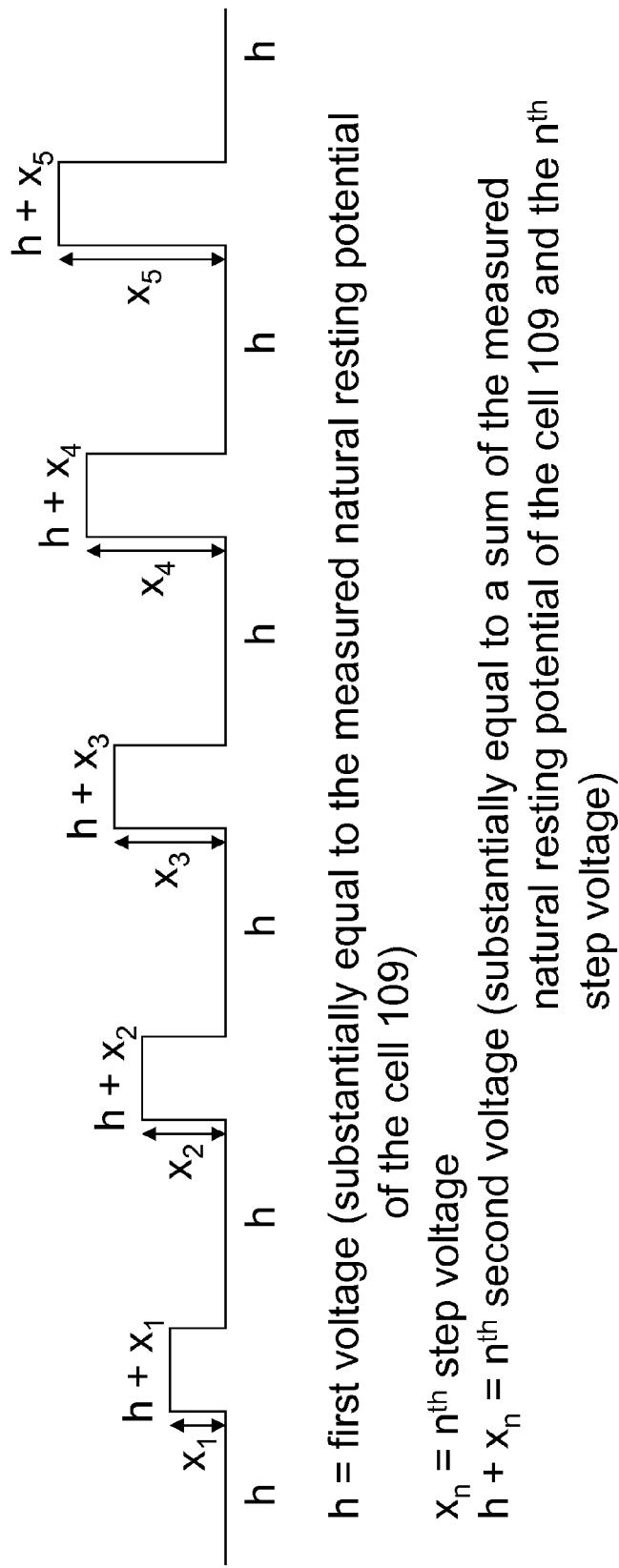
FIG. 17 illustrates an exemplary waveform of alternating voltages that may be applied to a cell in order to determine a characteristic thereof.

Switch 104 may then be opened to disconnect the sense amplifier 105 from the test head 140, and switch 108 may be closed to connect the voltage clamp amplifier 130 to the test head 140. At step 912, the clamp amplifier 130 may alternately apply to the cell 109 a first voltage substantially equal to the measured natural resting potential of the cell 109 and a second voltage substantially equal to a sum of the measured natural resting potential of the cell 109 and a step voltage (i.e., software 132 may employ controller 133 to alternate the voltage Vref applied to the non-inverting input of the clamp amplifier 130 between these first and second voltages). FIG. 17 illustrates one exemplary application of these alternating voltages. As shown, a different (e.g., increasing) step voltage may be applied on each application of the second voltage. The repetitive applications of the first voltage (depicted as voltage "h" in FIG. 17) between applications of the second voltage serves to rest the cell 109 between the applications of the second voltage.

In one embodiment, at step 916, the clamp amplifier 130 measures the characteristic of the cell 109. The measured characteristic of the cell 109 may be the current flowing through its membrane. In one embodiment, the clamp amplifier 130 measures the cell's membrane current during each application of the second voltage. The measured current may be recorded and stored in the memory 804 for later use and analysis.

As illustrated in FIG. 15, the sensing circuitry and clamping circuitry may each be coupled to a common single probe or electrode 110. In other words, the single probe or electrode 110 may be employed both to measure the natural resting potential of the cell 109 and to measure the characteristic of the cell 109.

The approach described above with reference to the method 900 does not require prior knowledge of the natural resting potential for the cell 109. Rather, the cell's natural resting potential is measured. In addition, as a result of measuring the cell's actual natural resting potential (rather than relying upon an approximate, and sometimes inaccurate, textbook value for a cell of a certain type), more accurate experimental data (e.g., measured values of the cell's membrane current) may be obtained. More specifically, by not relying upon an approximate textbook value for the cell's natural resting potential, the above-described approach avoid errors owing to differences in the natural resting potentials across individual cells of a given cell type.

F. Balancing Leak Current Compensation and Series Resistance (Rs) Compensation

Figure 2A:
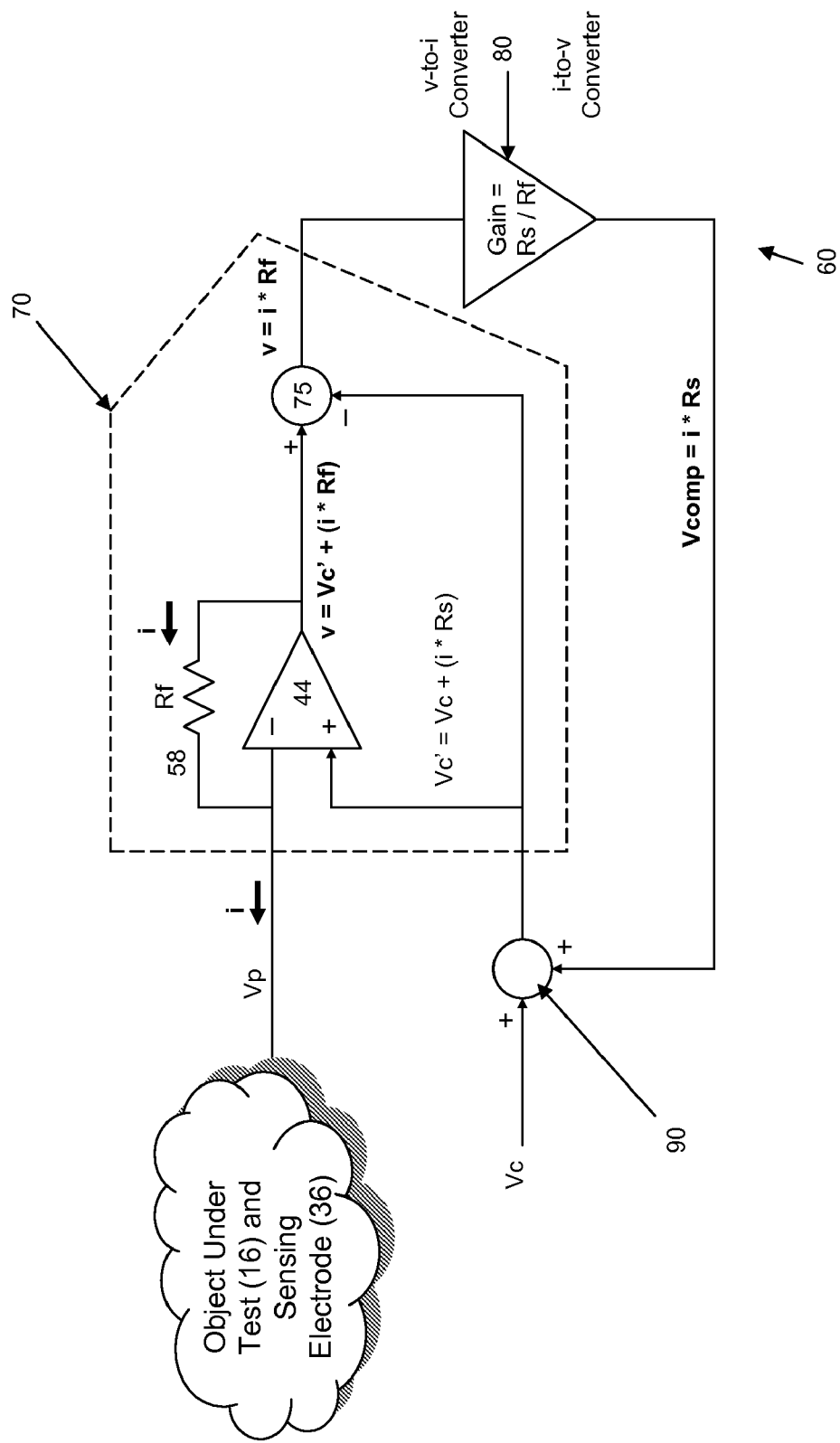
FIGS. 2A and 2B illustrate an exemplary Rs compensation circuit known to be used in patch clamp systems.
Figure 2B:
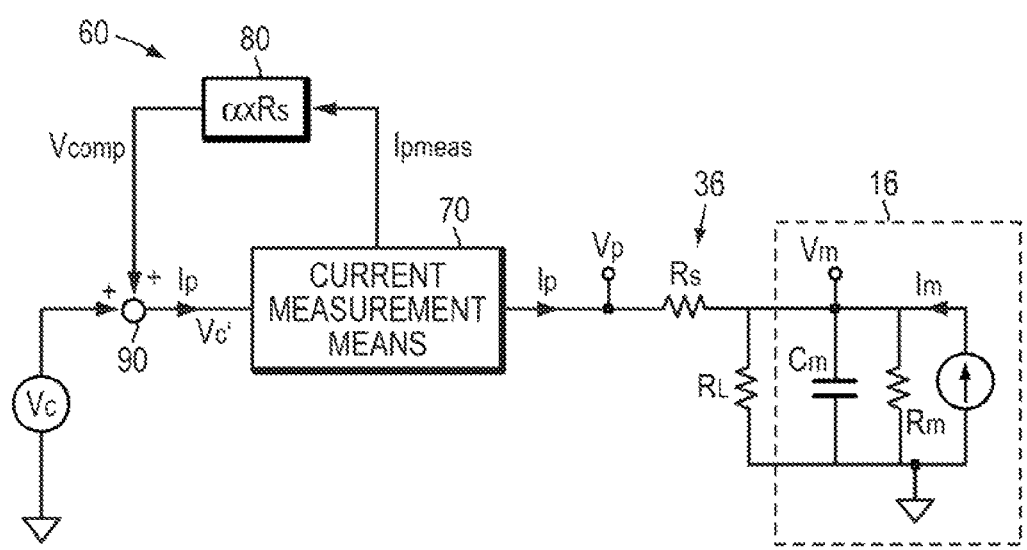

In one embodiment, in order to measure the characteristic of the cell 109 (e.g., the current flowing through the cell's membrane), the methods and systems described herein perform Rs compensation, such as the Rs compensation described above with reference to FIGS. 2A and 2B (or the Rs compensation described below with reference to FIGS. 19 and 20), and, in addition, leakage resistance compensation (or leak current compensation). The leak current compensation is performed to compensate for the leakage resistance introduced by the patch clamp system 100 while it measures the characteristic of the cell 109.

Figure 18:
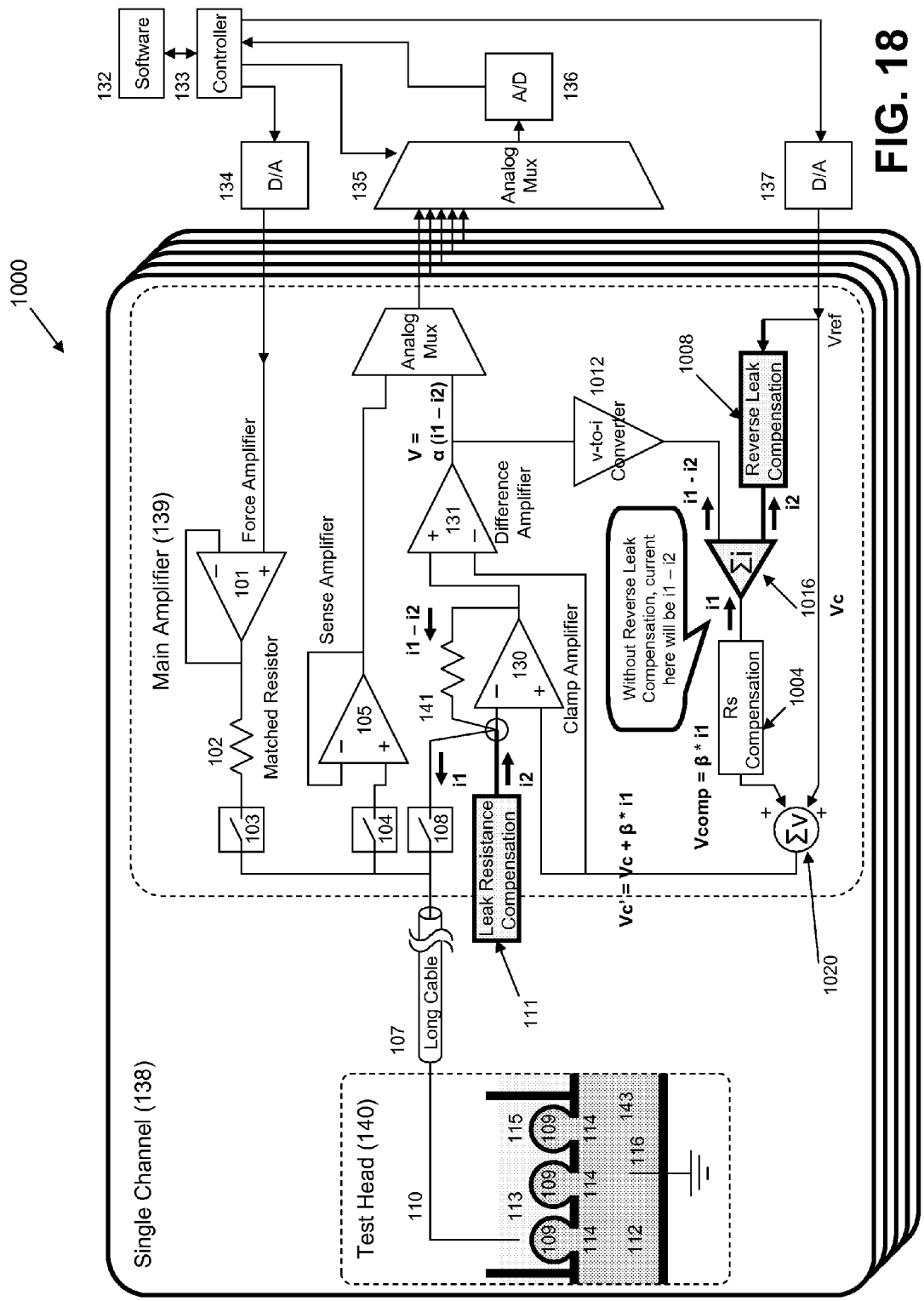
FIG. 18 is a circuit diagram of an embodiment of a single channel of the patch clamp system illustrated in FIG. 3 that performs both leak current compensation and Rs compensation.

FIG. 18 depicts one embodiment of a patch clamp system 1000 that performs both leak current compensation and Rs compensation. The patch clamp system 1000 may include all of the elements as described above with reference to FIG. 4 for the patch clamp system 100. For ease of illustration, components 117, 119, 120, 122, and 123 of the model circuitry, and components 125, 126, and 127 of the compensation circuitry, are not illustrated, but, as will be understood by one skilled in the art, they may be present in the patch clamp system 1000. In addition, as illustrated in FIG. 18, the patch clamp system 1000 may include Rs compensation circuitry 1004 to compensate for a series resistance introduced by the electrode 110, reverse leak compensation circuitry 1008, a voltage-to-current converter 1012, a current summer 1016, and a voltage summer 1020. The Rs compensation circuitry 1004 may be implemented as, for example, the scalar 80 described above with reference to FIGS. 2A and 2B. In addition, it is assumed in FIG. 18 that switch 142 connects current-to-voltage gain resistor 141 between the inverting input and the output of the voltage clamp amplifier 130. As such, switch 142 and current-to-voltage gain resistor 129 are not illustrated in FIG. 18.

In one embodiment, the leak resistance compensation circuitry 111 applies, to the measurement circuitry (i.e., the voltage clamp amplifier 130, the current-to-voltage gain resistor 141, and the difference amplifier 131), a first compensation signal (e.g., a compensation current) to compensate for the leakage resistance introduced by the patch clamp system 1000. Applying the first compensation signal to the measurement circuitry affects, however, the measured electrode 110 current. Since Rs compensation, such as the Rs compensation described above with reference to FIGS. 2A and 2B, relies on the measured electrode 110 current (or, as described above, the measured membrane current Im of the cell 109), performing this leak current compensation, without more, interferes with the Rs compensation. Accordingly, the methods and systems described herein further compensate, in one embodiment, the Rs compensation circuitry 1004 by applying yet another compensation signal to the Rs compensation circuitry 1004. This additional compensation signal removes from the measured electrode 110 current (or, as described above, the measured membrane current Im of the cell 109) that is applied to the Rs compensation circuitry 1004 the effect thereon of the first compensation signal.

In one exemplary mode of operation, a stimulus (e.g., a voltage) is applied to the cell(s) 109 through the electrode 110. A characteristic of the cell(s) 109, for example the current exhibited by the cell(s) 109, is then measured using the measurement circuitry. More specifically, with reference to FIG. 18, while the electrode current i1 is sensed, the leakage resistance compensation circuitry 111 applies to the measurement circuitry a first compensation signal, for example current i2, to compensate for the leakage resistance introduced into the patch clamp system 1000. Such leakage resistance may be introduced into the patch clamp system 1000 by, for example, the membrane resistance Rm of the cell(s) 109 and a seal resistance $R_L$ between the holder device (or chip) 113 and the cell(s) 109 (see, also, FIG. 2B). Accordingly, as illustrated in FIG. 18, the measured ionic current of the cell(s) 109 is in fact (i1−i2), i.e., the measured electrode current i1 less the current i2 applied to the measurement circuitry to compensate for the leakage resistance introduced by the patch clamp system 1000.

In addition, while measuring the ionic current exhibited by the cell(s) 109, the Rs compensation circuitry 1004 applies to the measurement circuitry, through the voltage summer 1020, a second compensation signal Vcomp to compensate for the series resistance introduced by the electrode 110. In one embodiment, the second compensation signal Vcomp applied to the measurement circuitry is related to the measured characteristic of the cell(s) 109, for example the measured ionic current (i1−i2) of the cell(s) 109, and to a third compensation signal. For example, in one embodiment, as illustrated in FIG. 18, a current substantially equal to the negative of the measured ionic current (i.e., −(i1−i2)) (output from the voltage-to-current converter 1012) and a third compensation signal (e.g., −i2) (output from the reverse leak compensation circuitry 1008) are applied to the Rs compensation circuitry 1004 through the current summer 1016. In such a fashion, the effect of the first compensation signal (i.e., i2), which is used in compensating for the leakage resistance introduced by the patch clamp system 1000, on the measured ionic current (i.e., i1−i2) of the cell(s) 109 is removed therefrom prior to use by the Rs compensation circuitry 1004. More specifically, as illustrated in FIG. 18, after addition by the current summer 1016 of the negative of the measured ionic current (i.e., −(i1−i2)) and the third compensation signal (e.g., −i2), only the negative of the electrode current (i.e., −i1) is considered by the Rs compensation circuitry 1004 in performing the Rs compensation, as would be the case without the leakage resistance compensation circuitry 111, the reverse leak compensation circuitry 1008, and the current summer 1016 present in the patch clamp system 1000. Thus, in accordance with one embodiment of the present invention, leak current compensation may be performed by the leakage resistance compensation circuitry 111 without interfering with the Rs compensation performed by the Rs compensation circuitry 1004.

G. Series Resistance (Rs) Compensation

Figure 19:
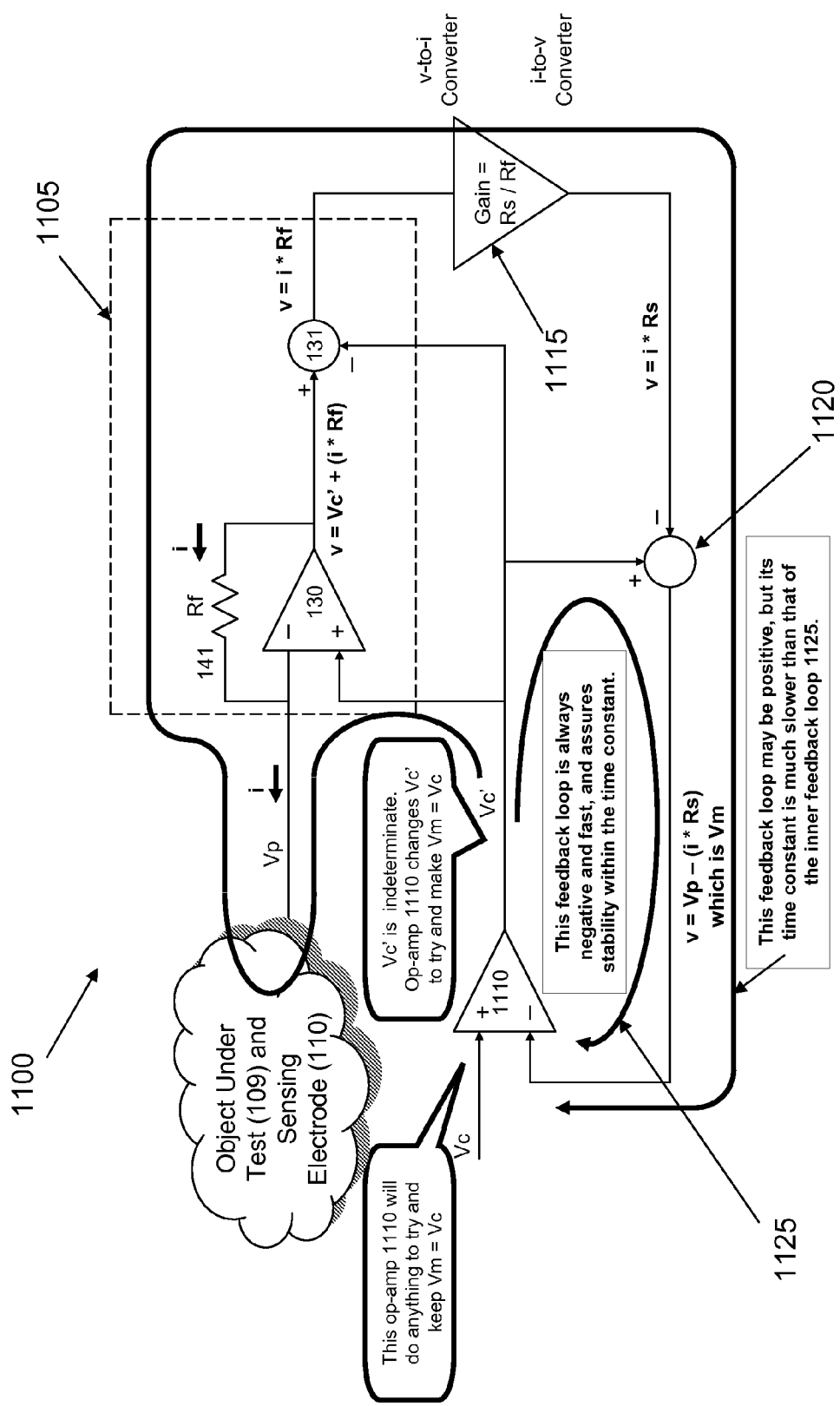
FIG. 19 is a circuit diagram of an Rs compensation circuit in accordance with one embodiment of the invention.

FIG. 19 depicts one embodiment of a system 1100 for compensating a series resistance of a device, such as the electrode 110, used in measuring a characteristic of an object under test, such as one or more of the cells 109 in an electrophysiological experiment. As illustrated, the system 1100 may include clamping circuitry 1105 as described above (i.e., voltage clamp amplifier 130, current-to-voltage gain resistor 141, and difference amplifier 131). The clamping circuitry 1105, as will be understood by one skilled in the art, applies a stimulus (i.e., a voltage substantially equal to Vc') to the cell(s) 109 through the sensing electrode 110 and measures a characteristic of the cell(s) 109, namely current i.

In one embodiment, to compensate for the series resistance Rs of the sensing electrode 110, the system 1100 further includes a scalar 1115 to provide a scaled version of the measured current i, an operational amplifier 1110 having an output coupled to an input of the clamping circuitry 1105 (i.e., to the non-inverting input terminal of the voltage clamp amplifier 130), and a subtractor 1120.

In one embodiment, as illustrated, the gain of the scalar 1115 is chosen to be equal to Rs/Rf, where Rs is the value of the series resistance for the sensing electrode 110 and Rf is the value of the resistance for the current-to-voltage gain resistor 141. In such a fashion, because the output of the clamping circuitry 1105 is iRf, the output from the scalar 1115 (and thus the input to the negative terminal of subtractor 1120) is iRs, which is equal to the voltage drop in the sensing electrode 110 due to its series resistance Rs.

As further illustrated in FIG. 19, through use of the subtractor 1120, the input to the inverting terminal of the operational amplifier 1110 is substantially equal to the output of the operational amplifier 1110 less the output from the scalar 1115, which, as just described, is a signal proportional to the measured current i of the cell(s) 109. However, because the output of the operational amplifier 1110 is also coupled to the non-inverting input of the voltage clamp amplifier 130, and because, as will be understood by one skilled in the art, the two input terminals of the voltage clamp amplifier 130 track each other in potential, the input to the positive terminal of the subtractor 1120 is substantially equal to the electrode voltage Vp and, thus, the input to the inverting terminal of the operational amplifier 1110 is Vp−iRs.

Referring back to FIG. 2B, it is readily seen, however, that Vp−iRs is equal to the membrane voltage Vm of the cell(s) 109. Thus, the input to the inverting terminal of the operational amplifier 1110 is the membrane voltage Vm of the cell(s) 109. Because the input to the non-inverting terminal of the operational amplifier 1110 is the command voltage Vc and because, as will be understood by one skilled in the art, the two input terminals of an operational amplifier track each other in potential, the operational amplifier 1110 will attempt to keep the membrane voltage Vm of the cell(s) 109 equal to Vc. Thus, by employing the system 1100 depicted in FIG. 19, one may clamp the membrane voltage Vm of the cell(s) 109 to the command voltage Vc. In addition, because the inner feedback loop 1125 of the system 1100 is negative, stability of the system 1100 is assured. Accordingly, the system 1100 is capable of providing substantially full (i.e., 100%) compensation of the undesired series resistance Rs in the sensing electrode 110.

Figure 20:
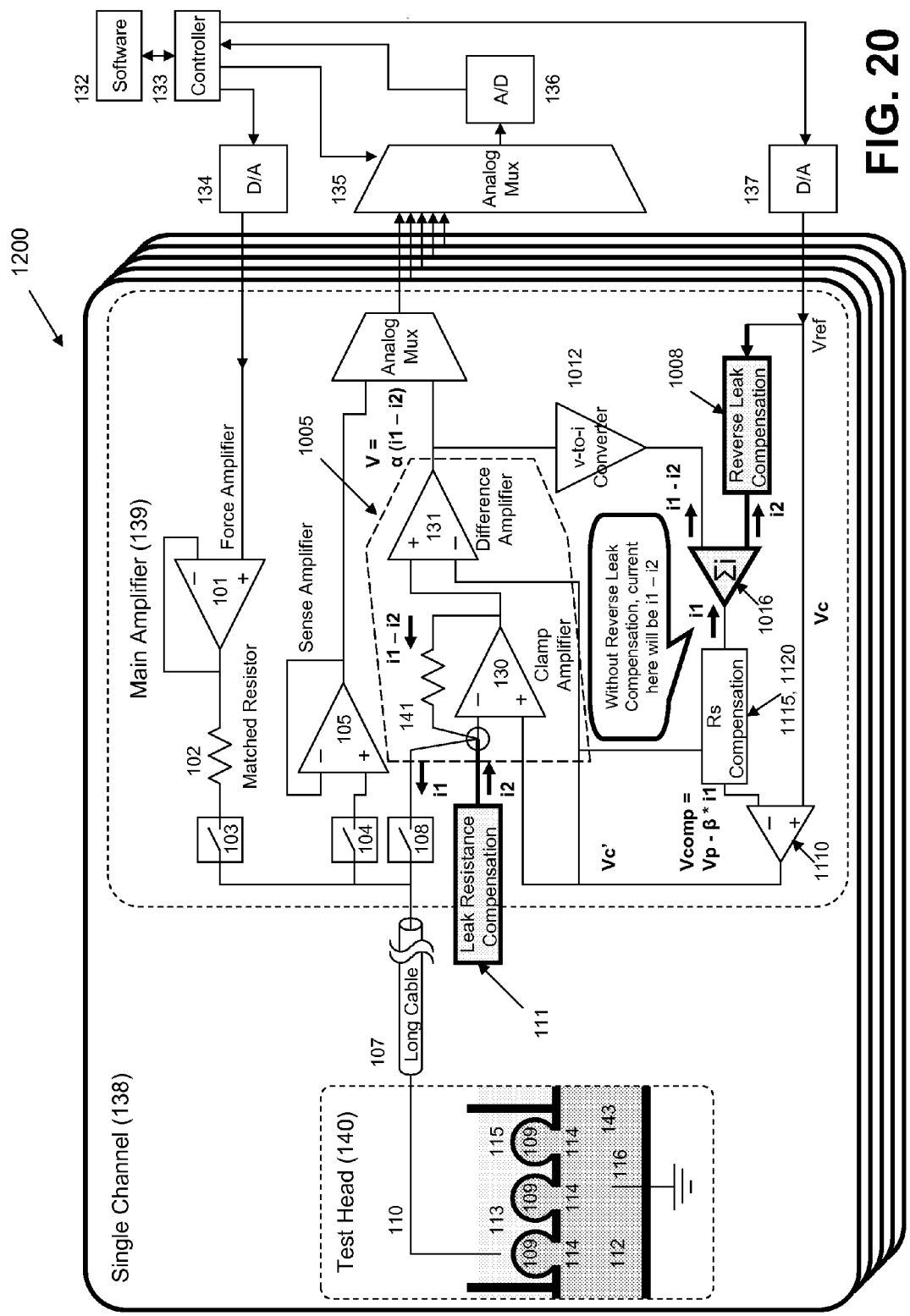
FIG. 20 is a circuit diagram of another embodiment of a single channel of the patch clamp system illustrated in FIG. 3 that performs both leak current compensation and Rs compensation.

As illustrated in FIG. 20, the system 1100 may be employed in a patch clamp system 1200 to provide Rs compensation to a measuring device 110, such as a probe or an electrode. In addition, as illustrated, the Rs compensation provided by the system 1100 may be utilized in conjunction with leak current compensation provided by leakage resistance compensation circuitry 111, as described above with reference to FIG. 18.

Certain embodiments of the present invention were described above. It is, however, expressly noted that the present invention is not limited to those embodiments, but rather the intention is that additions and modifications to what was expressly described herein are also included within the scope of the invention. Moreover, it is to be understood that the features of the various embodiments described herein were not mutually exclusive and can exist in various combinations and permutations, even if such combinations or permutations were not made express herein, without departing from the spirit and scope of the invention. In fact, variations, modifications, and other implementations of what was described herein will occur to those of ordinary skill in the art without departing from the spirit and the scope of the invention. As such, the invention is not to be defined only by the preceding illustrative description.

What is claimed is:

1. A method for compensating a patch clamp system used in electrophysiological experiments, the method comprising:
    calibrating, with at least one first calibration value, compensation circuitry to compensate for non-idealities introduced by analog model circuitry that models at least a portion of the patch clamp system;
    measuring a characteristic of at least one cell while employing the compensation circuitry, re-calibrated with at least one second calibration value, to compensate for non-idealities introduced by the patch clamp system; and
    following the measuring of the characteristic, verifying that the compensation circuitry, further re-calibrated with the at least one first calibration value, compensates for non-idealities introduced by the model circuitry.

2. The method of claim 1, wherein the compensation circuitry is calibrated, with the at least one first calibration value, to compensate for stray capacitances introduced by the model circuitry.

3. The method of claim 2, wherein the compensation circuitry is calibrated, with the at least one first calibration value, to compensate for a stray capacitance introduced by model circuitry of a long cable.

4. The method of claim 2, wherein the compensation circuitry is calibrated, with the at least one first calibration value, to compensate for a stray capacitance introduced by model circuitry of a long cable in series with a single cell.

5. The method of claim 2, wherein the compensation circuitry is calibrated, with the at least one first calibration value, to compensate for a stray capacitance introduced by model circuitry of a long cable in series with multiple cells.

6. The method of claim 1 further comprising activating the model circuitry prior to calibrating the compensation circuitry with the at least one first calibration value.

7. The method of claim 6 further comprising de-activating the model circuitry prior to measuring the characteristic of the at least one cell.

8. The method of claim 7 further comprising re-activating the model circuitry following the measuring of the characteristic of the at least one cell.

9. The method of claim 1, wherein the compensation circuitry is re-calibrated, with the at least one second calibration value and prior to measuring the characteristic of the at least one cell, to compensate for stray capacitances introduced by the patch clamp system.

10. The method of claim 9, wherein the compensation circuitry is re-calibrated, with the at least one second calibration value, to compensate for a stray capacitance introduced by a long cable in the patch clamp system.

11. The method of claim 9, wherein the compensation circuitry is re-calibrated, with the at least one second calibration value, to compensate for a stray capacitance introduced by a long cable in series with a single cell in the patch clamp system.

12. The method of claim 9, wherein the compensation circuitry is re-calibrated, with the at least one second calibration value, to compensate for a stray capacitance introduced by a long cable in series with multiple cells in the patch clamp system.

13. The method of claim 1, wherein the compensation circuitry is re-calibrated, with the at least one second calibration value and prior to measuring the characteristic of the at least one cell, to compensate for leakage resistance introduced by the patch clamp system.

14. The method of claim 1 further comprising measuring a stray capacitance introduced by at least one component in the patch clamp system.

15. The method of claim 14, wherein the at least one component comprises a long cable.

16. The method of claim 14, wherein the at least one component comprises a long cable in series with a single cell.

17. The method of claim 14, wherein the at least one component comprises a long cable in series with multiple cells.

18. The method of claim 14 further comprising comparing the measured stray capacitance to a capacitance modeled by the model circuitry to verify compensation for the non-idealities introduced by the patch clamp system.

19. The method of claim 18 further comprising discontinuing the measuring of the characteristic of the at least one cell if the measured stray capacitance differs from the capacitance modeled by the model circuitry by more than a predetermined amount.

20. The method of claim 1 further comprising comparing the first and second calibration values to verify compensation for the non-idealities introduced by the patch clamp system.

21. The method of claim 1, wherein the measured characteristic of the at least one cell is current.

22. The method of claim 1 further comprising increasing the gain of an amplifier employed in measuring the characteristic of the at least one cell after the compensation circuitry is re-calibrated with the at least one second calibration value.

23. A subsystem that compensates a patch clamp system used in electrophysiological experiments, the subsystem comprising:
    analog model circuitry that models at least a portion of the patch clamp system;
    compensation circuitry that compensates for non-idealities, the compensation circuitry compensating for non-idealities introduced by the model circuitry when calibrated with at least one first calibration value and compensating for non-idealities introduced by the patch clamp system when calibrated with at least one second calibration value;
    measurement circuitry that measures a characteristic of at least one cell while receiving input from the compensation circuitry to compensate for the non-idealities introduced by the patch clamp system; and
    a verification module that verifies, following the measurement of the characteristic, that the compensation circuitry, re-calibrated with the at least one first calibration value, compensates for the non-idealities introduced by the model circuitry.

24. The subsystem of claim 23, wherein the compensation circuitry is calibrated to compensate for stray capacitances introduced by the model circuitry.

25. The subsystem of claim 24, wherein the compensation circuitry is calibrated to compensate for a stray capacitance introduced by model circuitry of a long cable.

26. The subsystem of claim 24, wherein the compensation circuitry is calibrated to compensate for a stray capacitance introduced by model circuitry of a long cable in series with a single cell.

27. The subsystem of claim 24, wherein the compensation circuitry is calibrated to compensate for a stray capacitance introduced by model circuitry of a long cable in series with multiple cells.

28. The subsystem of claim 23, wherein the model circuitry activates prior to the compensation circuitry being calibrated with the at least one first calibration value.

29. The subsystem of claim 28, wherein the model circuitry de-activates prior to measuring the characteristic of the at least one cell with the measurement circuitry.

30. The subsystem of claim 29, wherein the model circuitry re-activates following the measuring of the characteristic of the at least one cell with the measurement circuitry.

31. The subsystem of claim 23, wherein the compensation circuitry is calibrated to compensate for stray capacitances introduced by the patch clamp system.

32. The subsystem of claim 31, wherein the compensation circuitry is calibrated to compensate for a stray capacitance introduced by a long cable in the patch clamp system.

33. The subsystem of claim 31, wherein the compensation circuitry is calibrated to compensate for a stray capacitance introduced by a long cable in series with a single cell in the patch clamp system.

34. The subsystem of claim 31, wherein the compensation circuitry is calibrated to compensate for a stray capacitance introduced by a long cable in series with multiple cells in the patch clamp system.

35. The subsystem of claim 23, wherein the compensation circuitry is calibrated to compensate for leakage resistance introduced by the patch clamp system.

36. The subsystem of claim 23, wherein the verification module compares a stray capacitance value measured from the patch clamp system to a capacitance value modeled by the model circuitry to verify compensation for the non-idealities introduced by the patch clamp system.

37. The subsystem of claim 36, wherein the measurement circuitry discontinues measuring the characteristic of the at least one cell if the measured stray capacitance value differs from the capacitance value modeled by the model circuitry by more than a predetermined amount.

38. The subsystem of claim 23, wherein the verification module compares the first and second calibration values to verify compensation for the non-idealities introduced by the patch clamp system.

39. The subsystem of claim 23, wherein the measured characteristic of the at least one cell is current.

40. The subsystem of claim 23, wherein the measurement circuitry comprises an amplifier having a gain, the gain being increased after the compensation circuitry is calibrated with the at least one second calibration value.

41. The subsystem of claim 23, wherein the subsystem is used with a patch clamp system comprising a test head, a main amplifier, and a long cable therebetween, and wherein the model circuitry, the compensation circuitry, and the measurement circuitry are all located within the main amplifier.

42. The subsystem of claim 41, further comprising ultra-low capacitance switches within the main amplifier.

43. A system for compensating a series resistance of a device used in measuring a characteristic of at least one cell in an electrophysiological experiment, the system comprising:
  clamping circuitry configured to i) apply a stimulus to the cell through the device and ii) measure the characteristic of the cell; and
  an operational amplifier having an output coupled to an input of the clamping circuitry, wherein an input to an inverting terminal of the operational amplifier is substantially equal to the output of the operational amplifier less a signal proportional to the measured characteristic of the cell.

44. The system of claim 43, wherein the device comprises an electrode.

45. The system of claim 43, wherein the measured characteristic comprises current.

* * * * *